US012661639B2

(12) United States Patent
Ooi

(10) Patent No.: US 12,661,639 B2
(45) Date of Patent: Jun. 23, 2026

(54) INORGANIC COMPOUND, DISPERSION AND METHOD FOR PRODUCING SAME, AND FILM AND METHOD FOR PRODUCING SAME, INORGANIC COMPOUND, METHOD FOR PRODUCING METHANE AND HYDROGEN, DISPERSION AND METHOD FOR PRODUCING SAME, AND FILM AND METHOD FOR PRODUCING SAME

(71) Applicant: JAPAN MATERIAL TECHNOLOGIES CORPORATION, Tokyo (JP)

(72) Inventor: Hirotaka Ooi, Tokyo (JP)

(73) Assignee: JAPAN MATERIAL TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 19/103,375

(22) PCT Filed: Aug. 17, 2023

(86) PCT No.: PCT/JP2023/029745
§ 371 (c)(1),
(2) Date: Feb. 12, 2025

(87) PCT Pub. No.: WO2024/038899
PCT Pub. Date: Feb. 22, 2024

(65) Prior Publication Data
US 2025/0256266 A1 Aug. 14, 2025

(30) Foreign Application Priority Data

Aug. 19, 2022 (JP) ................................. 2022-131218
Aug. 19, 2022 (JP) ................................. 2022-131219

(51) Int. Cl.
*B01J 27/22* (2006.01)
*B01J 35/40* (2024.01)
(Continued)

(52) U.S. Cl.
CPC ............... *B01J 27/22* (2013.01); *B01J 35/40* (2024.01); *B01J 37/0215* (2013.01);
(Continued)

(58) Field of Classification Search
CPC ........ B01J 2235/15; B01J 27/22; C01B 32/90
See application file for complete search history.

(56) References Cited

U.S. PATENT DOCUMENTS

2014/0291573 A1* 10/2014 Okada .................... C01G 49/10
252/182.1
2019/0181443 A1 6/2019 Ikeuchi et al.
(Continued)

FOREIGN PATENT DOCUMENTS

CN 104529455 A 4/2015
CN 104538597 A 4/2015
(Continued)

OTHER PUBLICATIONS

Fujihara, et al, "Sol-gel synthesis and luminescent properties of oxyfluoride LaOF: Eu3+ thin films." Journal of materials science letters 20.8 (2001): 687-689 (Year: 2001).*
(Continued)

*Primary Examiner* — Stuart L Hendrickson
*Assistant Examiner* — Eric Scott Sherman
(74) *Attorney, Agent, or Firm* — CANTOR COLBURN LLP

(57) ABSTRACT

This inorganic compound includes M, O, and F, in which M is one or more kinds of transition metal elements, when defining a molar ratio of O as "b" and defining a molar ratio of F as "c", (b/c) is 0.60 or more and 2.30 or less, and a
(Continued)

⊛ : Surface functional group atom

▨ : M atom

◯ : X atom half-value width of a diffraction peak of a (110) plane obtained by X-ray diffraction analysis is 0.60° or less. Also, the inorganic compound includes M, O, and F, in which M is one or more kinds of transition metal elements, when defining a molar ratio of O as "b" and defining a molar ratio of F as "c", (b/c) is 1.50 or less, and a half-value width of a diffraction peak of a (110) plane obtained by X-ray diffraction analysis is 0.45° or more.

18 Claims, 20 Drawing Sheets

(51) Int. Cl.

| | |
|---|---|
| *B01J 37/02* | (2006.01) |
| *C01B 3/042* | (2026.01) |
| *C01B 3/22* | (2006.01) |
| *C01B 32/90* | (2017.01) |
| *C07C 1/20* | (2006.01) |

(52) U.S. Cl.
CPC .............. *C01B 3/042* (2013.01); *C01B 3/22* (2013.01); *C01B 32/90* (2017.08); *C07C 1/20* (2013.01); *C01B 2203/0277* (2013.01); *C01B 2203/1041* (2013.01); *C01P 2002/50* (2013.01); *C01P 2002/72* (2013.01); *C01P 2002/74* (2013.01); *C01P 2002/88* (2013.01); *C01P 2004/03* (2013.01); *C01P 2006/80* (2013.01)

(56) References Cited

U.S. PATENT DOCUMENTS

| | | | |
|---|---|---|---|
| 2020/0091514 A1 | 3/2020 | Omae et al. | |
| 2020/0102444 A1 | 4/2020 | Cho et al. | |

FOREIGN PATENT DOCUMENTS

| | | |
|---|---|---|
| CN | 113181947 A | 7/2021 |
| JP | 2003229142 A | 8/2003 |
| JP | 2006172991 A | 6/2006 |
| JP | 2020093971 A | 6/2020 |
| WO | 2012177712 A1 | 12/2012 |
| WO | 2018092359 A1 | 5/2018 |
| WO | 2019064816 A1 | 4/2019 |

OTHER PUBLICATIONS

Hirai, et al. "Facile synthetic route to transition metal oxyfluorides via reactions between metal oxides and PTFE." Journal of Fluorine Chemistry 209 (2018): 43-48 (Year: 2018).*

Thapaliya, Bishnu P., et al. "Fluorination of MXene by Elemental F2 as Electrode Material for Lithium Ion Batteries." ChemSusChem 12.7 (2019): 1316-1324 (Year: 2019).*

Naguib, et al. "On the topotactic transformation of Ti2AIC into a Ti—C—O—F cubic phase by heating in molten lithium fluoride in air." Journal of the American Ceramic Society 94.12 (2011): 4556-4561 (Year: 2011).*

Reddy, et al. "Metal oxyfluorides TiOF2 and NbO2F as anodes for Li-ion batteries." Journal of power sources 162.2 (2006): 1312-1321 (Year: 2006).*

Hart, et al., "Control of MXenes' electronic properties through termination and intercalation, Nature communications," vol. 10 p. 1-10; https://doi.org/10.1038/s41467-018-08169-8; www.nature.com/naturecommunications.

International Search Report for International Application No. PCT/JP2023/029745; mailed Oct. 17, 2023.

PCT Written Opinion of the International Search Authority for International Application No. PCT/JP2023/029745; mailed Oct. 17, 2023.

* cited by examiner

○ : Surface functional group atom

◍ : M atom

○ : X atom

: Surface functional group atom

: M atom

: X atom

: Surface functional group atom

: $M^1$ atom

: $M^2$ atom

: $X^1$ atom

: $X^2$ atom

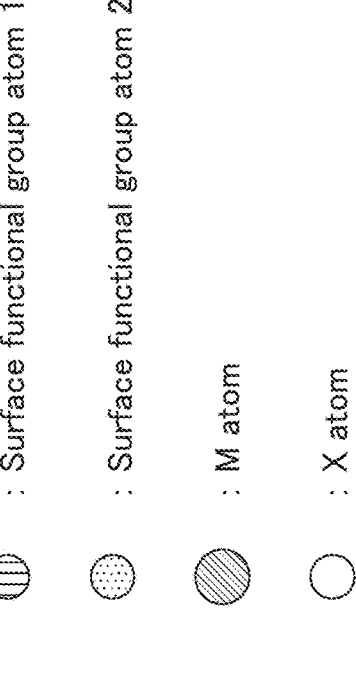
: Surface functional group atom 1
: Surface functional group atom 2
: M atom
: X atom
FIG. 4
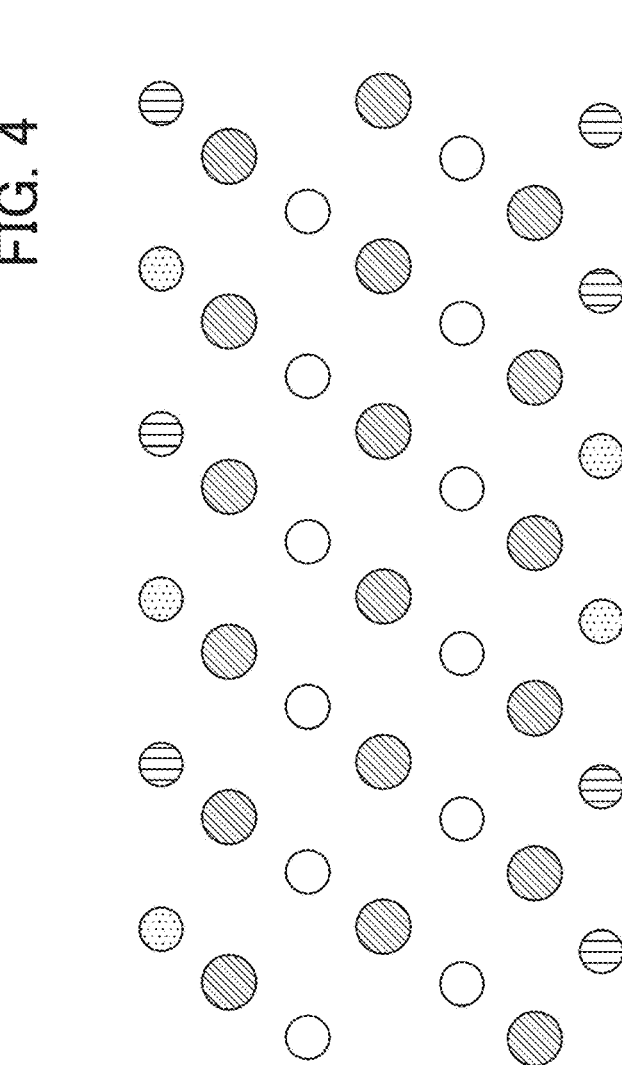

Temperature ° C

Wt %

Decomposition of weakly bonded surface functional group

Decomposition of strongly bonded surface functional group and crystals

INORGANIC COMPOUND, DISPERSION AND METHOD FOR PRODUCING SAME, AND FILM AND METHOD FOR PRODUCING SAME, INORGANIC COMPOUND, METHOD FOR PRODUCING METHANE AND HYDROGEN, DISPERSION AND METHOD FOR PRODUCING SAME, AND FILM AND METHOD FOR PRODUCING SAME

CROSS REFERENCE TO RELATED APPLICATIONS

This is the U.S. national stage of application No. PCT/JP2023/029745, filed on Aug. 17, 2023. Priority under 35 U.S.C. § 119 (a) and 35 U.S.C. § 365 (b) is claimed from Japanese Application No. 2022-131218, filed Aug. 19, 2022, and Japanese Application No. 2022-131219, filed Aug. 19, 2022, the disclosure of which is also incorporated herein by reference.

TECHNICAL FIELD

The present disclosure relates to an inorganic compound, a dispersion and a method for producing the same, as well as a film and a method for producing the same. In addition, the present disclosure relates to an inorganic compound, a method for producing methane and hydrogen, a dispersion and a method for producing the same, as well as a film and a method for producing the same.

BACKGROUND ART

Research into various inorganic compounds is being conducted actively. Among inorganic compounds, MXenes (MXene), which are composite atomic layer compounds, have been discovered and developed as a novel substance in recent years. MXenes are one kind of nanosheet material of which graphenes are representative, and are inorganic compounds represented by a compositional formula $M_{n+1}X_n$ as described in Patent Document 1, and having a part or all of a crystal structure in which M atoms and X atoms are arranged in a layered manner. M is a transition metal, and is exemplified by Sc, Y, Lu, Ti, Zr, Hf, V, Nb, Ta, Cr, Mo and W, for example. M may be constituted from one kind of transition metal or may be constituted from several kinds of transition metals. X is C and/or N. n is an integer from 1 to 4. In this way, MXenes have quite a number of variations according to the combinations of constituent elements. Depending on the combination of constituent elements, each of the MXenes has different physical properties and functions such as electroconductivity, catalytic activity, and stimulus response, and various MXenes have been studied depending on the application.

However, as described in Non-Patent Document 1, etc., for example, the conventionally reported MXenes are decomposed and reduced in weight by 20% or more when exposed to high temperatures. As described above, since the conventional MXenes have low heat resistance, it is difficult to apply as a material of an electronic component or a storage battery manufactured and used in a high temperature environment.

In addition, as a method for producing methane, in addition to methods which react carbon monoxide with hydrogen, methods which heat aluminum carbide, etc. have been known. However, high temperatures are a necessary condition of these methods for producing methane.

CITATION LIST

Patent Document

Patent Document 1: PCT International Publication No. WO2012/177712

Non-Patent Document

Non-Patent Document 1: James L. Hart, et al., Control of MXenes' electronic properties through termination and intercalation, nature communications, Vol. 10 pp. 1-10

DISCLOSURE OF THE INVENTION

Problems to be Solved by the Invention

An object of the present disclosure is to provide an inorganic compound having high heat resistance, a dispersion containing the inorganic compound and a method for producing the same, and a film containing the inorganic compound and a method for producing the same. In addition, it is object of the present disclosure to provide an inorganic compound capable of producing methane and hydrogen at a low temperature, a method for producing methane and hydrogen using the inorganic compound, a dispersion containing the inorganic compound and a method for producing the same, as well as a film containing the inorganic compound and a method for producing the same.

Means for Solving the Problems

[1] An inorganic compound includes M, O and F, in which M is one or more kinds of transition metal elements, when defining a molar ratio of O as "b" and defining a molar ratio of F as "c", (b/c) is 0.60 or more and 2.30 or less, and a half-value width of a diffraction peak of a (110) plane obtained by X-ray diffraction analysis is 0.600 or less.

[2] The inorganic compound as described in [1] further includes X, in which X is one or more kinds of elements selected from C and N.

[3] In the inorganic compound as described in [2], M is at least one of a group 4 element or a group 5 element in the periodic table, and X is C.

[4] In the inorganic compound as described in [2], M is at least one of Ti or Nb, and X is C.

[5] The inorganic compound as described in [1] further includes X and Y, in which X is one or more kinds of elements selected from C and N, and Y is one or more kinds of elements selected from the group consisting of H, an alkali metal element, an alkaline earth metal element, a chalcogen element excluding oxygen, and a halogen element excluding fluorine.

[6] In the inorganic compound as described in [4], M is at least one of a group 4 element or a group 5 element in the periodic table, and X is C.

[7] In the inorganic compound as described in [4], M is at least one of Ti or Nb, and X is C.

[8] The inorganic compound as described in any one of [1] to [7] further includes one or more kinds of inevitable impurities selected from the group consisting of Al, Si, Ga, P, S, Ge, As, Cd, In, Sn, Tl and Pb, in which a ratio (Wi/Wm)

of a total molar amount Wi of the inevitable impurities relative to a total molar amount Wm of M is $1.0 \times 10^{-6}$ or more and $5.0 \times 10^{-1}$ or less.

[9] In the inorganic compound as described in any one of [1] to [8], when defining a molar ratio of M in the inorganic compound as "a", ((b+c)/a) is 0.30 or more.

[10] In the inorganic compound as described in any one of [1] to [9], when defining a molar ratio of M in the inorganic compound as "a", ((b+c)/a) is 1.60 or less.

[11] In the inorganic compound as described in any one of [1] to [10], the inorganic compound is in a layered form, and a thickness of a layer thereof is 0.15 μm or more and 10.00 μm or less.

[12] In the inorganic compound as described in any one of [1] to [11], a weight ratio of HF in the inorganic compound relative to a total amount of the inorganic compound is 1 ppt or more and 50 ppm or less.

[13] In the inorganic compound as described in any one of [1] to [12], a weight ratio of moisture in the inorganic compound relative to a total amount of the inorganic compound is 1 ppm or more and 1.0% or less.

[14] In the inorganic compound as described in any one of [1] to [13], the inorganic compound is a MXene.

[15] A dispersion includes the inorganic compound as described in any one of [1] to [14].

[16] A film includes the inorganic compound as described in any one of [1] to [14].

[17] A method for producing a dispersion includes producing the dispersion using the inorganic compound as described in any one of [1] to [14].

[18] A method for producing a film includes producing the film using the inorganic compound as described in any one of [1] to [14].

[19] An inorganic compound includes M, O and F, in which M is one or more kinds of transition metal elements, when defining a molar ratio of O as "b" and defining a molar ratio of F as "c", (b/c) is 1.50 or less, and a half-value width of a diffraction peak of a (110) plane obtained by X-ray diffraction analysis is 0.450 or more.

[20] The inorganic compound as described in [19] further includes X, in which X includes at least C among C and N.

[21] In the inorganic compound as described in [20], M is Ti, and X is C.

[22] The inorganic compound as described in [19], further includes X and Y, in which X includes at least C among C and N, and Y is one or more kinds of elements selected from the group consisting of H, an alkali metal element, an alkaline earth metal element, a chalcogen element excluding oxygen, and a halogen element excluding fluorine.

[23] In the inorganic compound as described in [22], M is Ti, and X is C.

[24] The inorganic compound as described in any one of [19] to [23], further includes one or more kinds of elements selected from the group consisting of Al, Si, Ga, P, S, Ge, As, Cd, In, Sn, Tl and Pb, in which a ratio (Wi/Wm) of a total molar amount Wi of the elements relative to a total molar amount Wm of M is 0.03 or more and 0.50 or less.

[25] In the inorganic compound as described in any one of [19] to [24], when defining a molar ratio of M in the inorganic compound as "a", ((b+c)/a) is 0.50 or more.

[26] In the inorganic compound as described in any one of [19] to [25], the inorganic compound is in a layered form, and a thickness of a layer thereof is 0.20 μm or less.

[27] In the inorganic compound as described in any one of [19] to [26], the inorganic compound is a MXene.

[28] A method for producing methane and hydrogen includes heating the inorganic compound as described in any one of [19] to [27] to produce methane and hydrogen.

[29] A method for producing methane and hydrogen includes bringing the inorganic compound as described in any one of [19] to [27] into contact with an alcohol or water to produce methane and hydrogen.

[30] A dispersion includes the inorganic compound as described in any one of [19] to [27].

[31] A film includes the inorganic compound as described in any one of [19] to [27].

[32] A method for producing a dispersion includes producing the dispersion using the inorganic compound as described in any one of [19] to [27].

[33] A method for producing a film includes producing the film using the inorganic compound as described in any one of [19] to [27].

Effects of the Invention

According to the present disclosure, it is possible to provide an inorganic compound having high heat resistance, a dispersion containing the inorganic compound and a method for producing the same, and a film containing the inorganic compound and a method for producing the same. In addition, according to the present disclosure, it is possible to provide an inorganic compound capable of producing methane and hydrogen at a low temperature, a method for producing methane and hydrogen using the inorganic compound, a dispersion containing the inorganic compound and a method for producing the same, as well as a film containing the inorganic compound and a method for producing the same.

BRIEF DESCRIPTION OF THE DRAWINGS

FIG. 4 is a schematic diagram showing an example of a crystal structure of a MXene including a plurality of kinds of surface functional group atoms.

PREFERRED MODE FOR CARRYING OUT THE INVENTION

Figure 1:
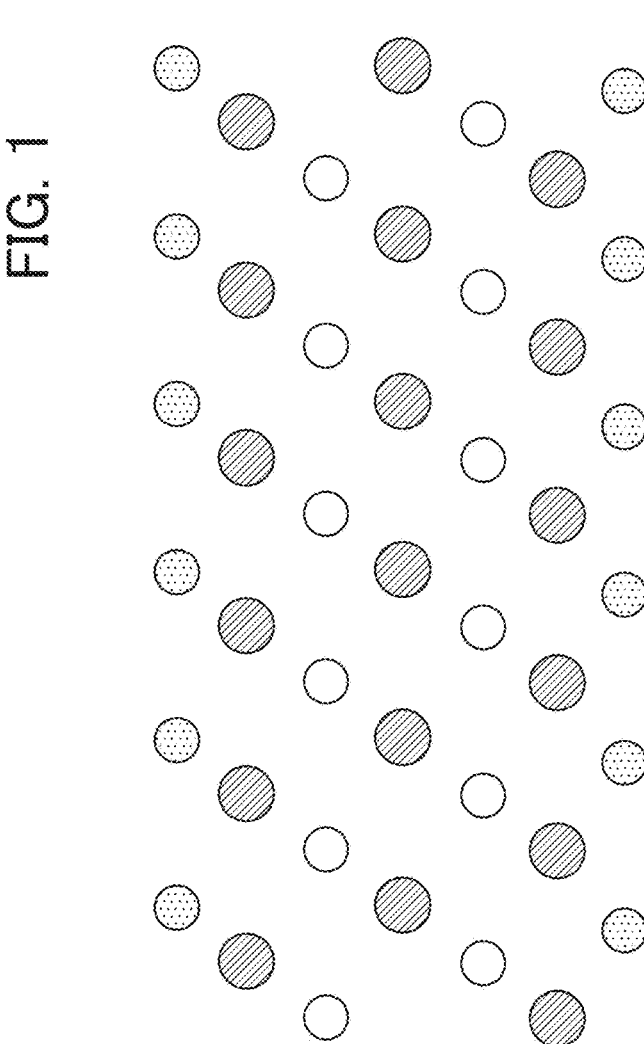
FIG. 1 is a schematic diagram showing an example of a crystal structure of a MXene.

Hereinafter, the present invention will be described in detail based on embodiments.

As a result of intensive studies, the present inventors have found that the composition and crystallite size of an inorganic compound are controlled to increase heat resistance by a manufacturing condition different from the conventional way, thereby arriving at completion of the present disclosure based on such findings. In addition, as a result of intensive studies, the present inventors have found that the composition and crystallite size of an inorganic compound are controlled to produce methane and hydrogen at a low temperature by a manufacturing condition different from the conventional way, thereby arriving at completion of the present disclosure based on such findings.

First Embodiment

An inorganic compound according to a first embodiment includes M, O, and F, in which M is one or more kinds of transition metal elements, (b/c) is 0.60 or more and 2.30 or less when defining the molar ratio of O as "b" and defining the molar ratio of F as "c", and the half-value width of the diffraction peak of the (110) plane obtained by X-ray diffraction analysis is 0.600 or less.

As described above, the inorganic compound of the first embodiment includes M, O (oxygen), and F (fluorine).

M constituting the inorganic compound is one or more kinds of transition metal elements and is preferably an early transition metal element. For example, M may be one kind of transition metal element or may be two or more kinds of transition metal elements.

The inorganic compound may further include X in addition to M, O, and F. X constituting the inorganic compound is one or more kinds of elements selected from C (carbon) and N (nitrogen). That is, X is C only, N only, or C and N.

When the inorganic compound includes M, O, F, and X, M is preferably at least one of a group 4 element or a group 5 element in the periodic table, and more preferably at least one of Ti (titanium) or Nb (niobium), from the viewpoint of improving the heat resistance of the inorganic compound. Furthermore, from the same viewpoint, X is preferably C.

The inorganic compound may further include X and Y in addition to M, O, and F. Y constituting the inorganic compound is one or more kinds of elements selected from the group consisting of H (hydrogen), an alkali metal element, an alkaline earth metal element, a chalcogen element excluding oxygen, and a halogen element excluding fluorine. For example, Y may be one kind of alkali metal element or may be one kind of alkali metal element and one kind of alkaline earth metal element. Y is preferably one or more kinds of elements selected from the group consisting of H, Li, Na, K, Be, Mg, Ca, Sr, Ba, Ra, S, Se, Te, Cl, Br and I, more preferably one or more kinds of elements selected from the group consisting of H, Li, Na, K, Mg, Ca, S, Se, Cl and Br, and still more preferably one or more kinds of elements selected from the group consisting of H, Li, Na and Cl.

When the inorganic compound includes M, O, F, X, and Y, M is preferably at least one of a group 4 element or a group 5 element in the periodic table, and more preferably at least one of Ti or Nb, from the viewpoint of improving the heat resistance of the inorganic compound. Furthermore, from the same viewpoint, X is preferably C.

The inorganic compound may include one or more kinds of elements selected from the group consisting of Al, Si, Ga, P, S, Ge, As, Cd, In, Sn, Tl, and Pb as inevitable impurities. Inevitable impurity is an impurity at a content level that is inevitably mixed in the manufacturing process. Depending on the content of the inevitable impurities, it may be a factor affecting the characteristics of the inorganic compound, and therefore, the content of the inevitable impurities is preferably small.

From the viewpoint of maintaining the improvement in the heat resistance of the inorganic compound, the ratio (Wi/Wm) of the total molar amount Wi of the inevitable impurities relative to the total molar amount Wm of M contained in the inorganic compound is preferably $5.0\times10^{-1}$ or less and is preferably as small as possible. In addition, the lower limit of the ratio (Wi/Wm) is, for example, $1.0\times10^{-6}$ or more.

In addition, the inorganic compound may include an element other than the above-mentioned elements to an extent such that the effect of improving the heat resistance of the inorganic compound is not reduced.

In addition, the inorganic compound is preferably a layered inorganic compound (hereinafter, it is also referred to as a layered compound), and thereamong, is more preferably a MXene. The layered inorganic compound is an inorganic compound in which primary particles or secondary particles of the inorganic compound have a sheet shape.

Suitable layered compounds include clay minerals such as smectites, magadiite, kanemite, talc and kaolinite; niobates such as potassium niobate and lithium niobate; titanates such as potassium titanate and lithium titanate; metal phosphates; layered hydroxides such as hydrotalcite; metal chalcogenides such as $MoS_2$, $WS_2$, $TaS_2$ and $NbS_2$; MXenes and MAX phases.

Figure 2:
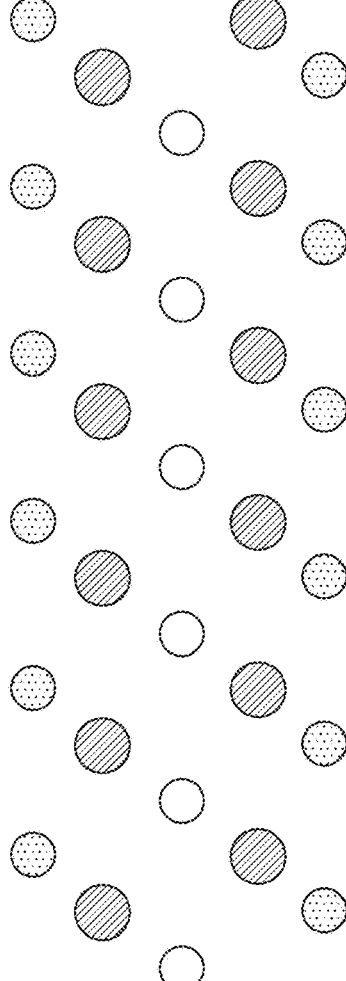
FIG. 2 is a schematic diagram showing another example of a crystal structure of a MXene.
Figure 3:
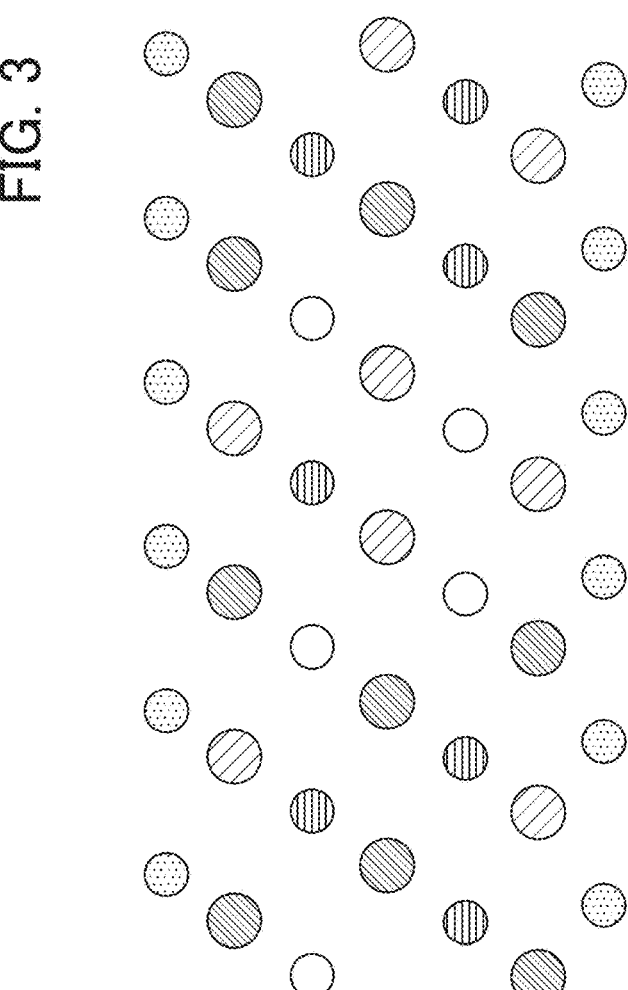
FIG. 3 is a schematic diagram showing an example of a crystal structure of a MXene including a plurality of kinds of M elements and a plurality of kinds of X elements.

In addition, MXene is an inorganic compound generally represented by the compositional formula $M_{n+1}X_n$ (n is an integer of 1 to 4) and having a part or all of a crystal structure in which M atoms and X atoms are arranged in a layered manner, and FIGS. 1 to 4 are exemplified thereas, for example. FIG. 1 is a schematic diagram showing an example of the crystal structure of a $M_3X_2$ MXene. It has a structure in which layers of M atoms and layers of X atoms are alternately arranged and has surface functional group atoms on the outermost surface. FIG. 2 is a schematic diagram showing an example of the crystal structure of a $M_2X$ MXene. Although the number of layers is different from that of a $M_3X_2$ MXene, a $M_2X$ MXene also has a similar structure. FIG. 3 is a schematic diagram showing an example of a crystal structure of a MXene having a plurality of kinds of M elements and a plurality of kinds of X elements. FIG. 4 is a schematic diagram showing an example of a crystal structure of a MXene having a plurality of kinds of surface functional group atoms.

In addition, the MAX phase is an inorganic compound represented by the compositional formula $M_{n+1}AX_n$. For example, n is an integer from 1 to 4.

In the case of the inorganic compound according to the first embodiment being a MXene including M, O, F, and X, the MXene is represented by the following formula (1) when defining the molar ratio of M included in the inorganic compound as "a", the molar ratio of O as "b", the molar ratio of F as "c", and the molar ratio of X as "d". When X is composed of C and N, the molar ratio of C is represented by d1, and the molar ratio of N is represented by d2. The sum of d1 and d2 (d1+d2) is d.

$$M_a X_d O_b F_c \qquad \text{Formula (1)}$$

As the MXenes represented by the formula (1), $Ti_a C_d O_b F_c$, $Ti_a N_d O_b F_c$, $Ti_a C_{d1} N_{d2} O_b F_c$, $V_a C_d O_b F_c$, $V_a N_d O_b F_c$, $V_a C_{d1} N_{d2} O_b F_c$, $Nb_a C_d O_b F_c$, $Nb_a N_d O_b F_c$, $Nb_a C_{d1} N_{d2} O_b F_c$, $MO_a C_d O_b F_c$, $MO_a N_d O_b F_c$, $MO_a C_{d1} N_{d2} O_b F_c$, $Sc_a C_d O_b F_c$, $Sc_a N_d O_b F_c$, $Sc_a C_{d1} N_{d2} O_b F_c$, $Cr_a C_d O_b F_c$, $Cr_a N_d O_b F_c$, $Cr_a C_{d1} N_{d2} O_b F_c$, $Zr_a C_d O_b F_c$, $Zr_a N_d O_b F_c$, $Zr_a C_{d1} N_{d2} O_b F_c$, $Hf_a C_d O_b F_c$, $Hf_a N_d O_b F_c$, $Hf_a C_{d1} N_{d2} O_b F_c$, $Ta_a C_d O_b F_c$, $Ta_a N_d O_b F_e$ and $Ta_a C_{d1} N_{d2} O_b F_c$ are preferable from the viewpoint of heat resistance improvement and ease of synthesis, among them, $Ti_a C_d O_b F_e$, $Ti_a N_d O_b F_c$, $Ti_a C_{d1} N_{d2} O_b F_c$, $V_a C_d O_b F_c$, $V_a N_d O_b F_c$, $V_a C_{d1} N_{d2} O_b F_c$, $Nb_a C_d O_b F_c$, $Nb_a N_d O_b F_c$, $Nb_a C_{d1} N_{d2} O_b F_c$, $MO_a C_d O_b F_c$, $MO_a N_d O_b F_c$, $MO_a C_{d1} N_{d2} O_b F_c$, $Cr_a C_d O_b F_c$, $Cr_a N_d O_b F_c$, $Cr_a C_{d1} N_{d2} O_b F_c$, $Ta_a C_d O_b F_c$, $Ta_a N_d O_b F_e$ and $Ta_a C_{d1} N_{d2} O_b F_c$ are more preferable from the viewpoint of further having high functions such as electroconductivity and catalytic function, and among them, $Ti_a C_{d1} N_{d2} O_b F_c$, $V_a C_d O_b F_c$, $V_a N_d O_b F_c$, $V_a C_{d1} N_{d2} O_b F_c$, $Nb_a C_d O_b F_c$, $Nb_a N_d O_b F_c$ and $Nb_a C_{d1} N_{d2} O_b F_c$ are more preferable from the viewpoint of further improving the above functions.

In addition, when the inorganic compound is a MXene including M, O, F, X, and Y, the MXene is represented by the following formula (2), when defining the molar ratio of M included in the inorganic compound as "a", the molar ratio of 0 as "b", the molar ratio of F as "c", the molar ratio of X as "d", and the molar ratio of Y as "e". When Y is composed of n kinds of elements of Y1 to Yn (n is an integer of 1 or more), the molar ratios of the respective elements of Y are represented by e1 to en, respectively. The sum of e1 to en (e1+ . . . +en) is e.

$$M_a X_d O_b F_c Y_e \qquad \text{Formula (2)}$$

From the viewpoint of improving the heat resistance of the inorganic compound, as the MXene represented by the formula (2), Y preferably includes one or more kinds of elements selected from the group consisting of H, Li, Na, K, Be, Mg, Ca, Sr, Ba, Ra, S, Se, Te, Cl, Br and I, more preferably includes one or more kinds of elements selected from the group consisting of H, Li, Na, K, Mg, Ca, S, Se, Cl and Br, and still more preferably includes one or more kinds of elements selected from the group consisting of H, Li, Na and Cl. Specific examples of the MXene represented by the formula (2) include $Ti_a C_d O_b F_c H_e$, $Ti_a N_d O_b F_c H_e$, $Ti_a C_{d1} N_{d2} O_b F_c H_e$, $Ti_a C_d O_b F_c H_{e1} Li_{e2}$, $Ti_a N_d O_b F_c H_{e1} Li_{e2}$, $Ti_a C_{d1} N_{d2} O_b F_c H_{e1} Li_{e2}$, $Ti_a C_d O_b F_c H_{e1} Cl_{e2}$, $Ti_a N_d O_b F_c H_{e1} Cl_{e2}$, $Ti_a C_{d1} N_{d2} O_b F_c H_{e1} Cl_{e2}$ and $Nb_a C_d O_b F_c H_e$.

For the inorganic compound, when defining the molar ratio of 0 included in the inorganic compound as "b" and the molar ratio of F as "c", (b/c) is 0.60 or more and 2.30 or less. When (b/c) is within the above range, the heat resistance of the inorganic compound can be improved.

In addition, when defining the molar ratio of M included in the inorganic compound as "a", ((b+c)/a) is preferably 1.60 or less. When ((b+c)/a) is within the above range, the heat resistance of the inorganic compound can be further improved.

In particular, from the viewpoint of improving the heat resistance of the inorganic compound from room temperature to 350° C., (b/c) is 0.60 or more, preferably 1.10 or more, more preferably 1.30 or more, and still more preferably 1.70 or more. From the same viewpoint, the upper limit of ((b+c)/a) is preferably 1.60 or less, more preferably 1.20 or less, and even more preferably 1.00 or less, and the lower limit of ((b+c)/a) is preferably 0.30 or more, and more preferably 0.70 or more. In addition, from the viewpoint of improving the heat resistance of the inorganic compound at 350° C. or higher, (b/c) is 2.30 or less, preferably 2.10 or less, more preferably 1.80 or less, and still more preferably 1.40 or less. From the same viewpoint, the upper limit of ((b+c)/a) is preferably 1.60 or less, and the lower limit of ((b+c)/a) is preferably 0.30 or more, more preferably 0.70 or more, still more preferably 1.00 or more, and particularly preferably 1.20 or more.

The weight reduction of the inorganic compound from room temperature to 350° C. is considered to be due to decomposition and volatilization of weakly bonded surface functional group atoms mainly present on the surface of the inorganic compound. Since the heat resistance of the inorganic compound is higher with a smaller ((b+c)/a) representing the total amount of functional groups, and the amount of M-F bonds which are relatively weak bonds is smaller with a larger (b/c) representing the ratio of the kinds of functional groups, the heat resistance of the inorganic compound is improved. Further, the weight reduction of the inorganic compound at 350° C. or higher is the decomposition of the strongly bonded surface functional groups and the decomposition of the bulk portion of the inorganic compound, and it is considered that the heat resistance of the inorganic compound becomes higher with fewer defects and less strain of the inorganic compound. When (b/c) and ((b+c)/a) are within the above ranges, an inorganic compound having few defects and less strain can be obtained, and thus the heat resistance of the inorganic compound is improved.

The molar ratio a of M, the molar ratio b of O, and the molar ratio c of F contained in the inorganic compound can be measured by SEM-EDX.

In addition, the half-value width of the diffraction peak of the (110) plane obtained by X-ray diffraction analysis of the inorganic compound (hereinafter also simply referred to as half-value width) is 0.600 or less, preferably 0.540 or less, more preferably 0.400 or less, and is preferably as small as possible. When the half-value width is 0.600 or less, the heat resistance of the inorganic compound can be improved, and the heat resistance of the inorganic compound can be improved with a smaller half-value width. It is considered that decomposition of the inorganic compound occurs from a defect or a strained portion of a crystal, and when the half-value width is small, that is, when the single crystal size is large and the number of defects is small, it is considered that the inorganic compound will hardly decompose, and thus the heat resistance is increased. In addition, the lower limit of the half-value width is, for example, 0.0010 or more.

The X-ray diffraction analysis of the inorganic compound is performed as follows. Using an X-ray diffractometer, the sample holder is filled with a powdered inorganic compound, the X-ray diffraction intensity between, for example, 3° and 80° is measured by the θ-2θ method, and the background value, which is noise, is subtracted from the peak intensity to obtain the diffraction peak of the (110) plane. Based on the obtained diffraction peak of the (110) plane, the half-value width is calculated. At this time, a characteristic X-ray (wavelength: 0.154 nm) of CuKα is used as the X-ray.

In addition, the inorganic compound is preferably in a layered form, and the lower limit for the thickness of the layer is preferably 0.15 μm or more, more preferably 0.18 μm or more, and even more preferably 0.20 μm or more, and the upper limit thereof is preferably 10.00 μm or less, more preferably 5.00 μm or less, and even more preferably 2.00 μm or less. When the thickness of the layer of the inorganic compound is 0.15 μm or more, the heat resistance of the inorganic compound is improved. In addition, when the thickness of the layer of the inorganic compound is 10.00 μm or less, a sheet-like form can be obtained, and the effects such as an increase in specific surface area can be obtained.

The thickness of the layer of the inorganic compound is not the thickness of a single crystal sheet (sheet-shaped single crystal) of the inorganic compound, but rather the thickness of a sheet-shaped aggregate obtained by stacking a plurality of single crystal sheets of the inorganic compound via a gap of approximately 0.05 μm or less. The shape of the inorganic compound and the thickness of the layer of the inorganic compound are measured by observing the powdered inorganic compound with a scanning electron microscope (SEM).

In addition, in the case where hydrogen fluoride (HF) is contained in the inorganic compound, the weight ratio of HF in the inorganic compound relative to the total amount of the inorganic compound (hereinafter also simply referred to as the weight ratio of HF) is preferably 50 ppm or less, more preferably 20 ppm or less, still more preferably 10 ppm or less, and is preferably as small as possible. When the weight ratio of HF is 50 ppm or less, the heat resistance of the inorganic compound can be further improved, and the heat resistance of the inorganic compound can be improved with a smaller weight ratio of HF. The lower limit of the weight ratio of HF is, for example, 1 ppt or more.

The weight ratio of HF can be determined by mixing the inorganic compound and an organic solvent that can dissolve HF, and stirring the mixture for 24 hours, then measuring the F ion concentration in the organic solvent by ion chromatography to quantify the HF weight extracted in the organic solvent and dividing the HF weight by the weight of the inorganic compound.

In addition, in the case where moisture is contained in the inorganic compound, the weight ratio of moisture in the inorganic compound relative to the total amount of the inorganic compound (hereinafter also simply referred to as the weight ratio of moisture) is preferably 1.0% or less, more preferably 0.5% or less, still more preferably 0.10% or less, and is preferably as small as possible. When the weight ratio of moisture is 1.0% or less, the heat resistance of the inorganic compound can be further improved, and the heat resistance of the inorganic compound can be improved with a smaller weight ratio of moisture. In addition, the lower limit of the weight ratio of moisture is, for example, 1 ppm or more.

The weight ratio of moisture can be determined by mixing the inorganic compound and an organic solvent miscible with water, stirring the mixture for 24 hours, quantifying the weight of moisture in the organic solvent by a Karl Fischer moisture meter or the like, and dividing the weight of moisture by the weight of the inorganic compound.

Since such an inorganic compound of the first embodiment is excellent in heat resistance, it can be suitably used as a material of an electronic component or a storage battery manufactured and used in a high temperature environment, in which it has been difficult to apply a conventional MXene having low heat resistance. Furthermore, the inorganic compound can be suitably used as a material of a solar cell, an LED, or a touch panel.

Next, an example of a method for producing the inorganic compound according to the first embodiment will be described.

For example, a MAX phase (max phase) is added to a solution for selectively removing the A phase (hereinafter also referred to as a removal solution), and the A phase of the MAX phase is selectively removed, thereby generating aggregates in which a nano-sized single crystal sheet mainly composed of M and X and a plurality of the single crystal sheets are stacked. Thereafter, the aggregates generated in the solution are washed and dried to obtain powdery aggregates. This process itself is a common method of producing conventional MXenes. Here, A is a group 13 element or a group 14 element of the periodic table. The removal solution is preferably hydrofluoric acid which is a hydrogen fluoride (HF) solution. In addition, the removal solution may be a mixed solution obtained by mixing hydrofluoric acid with another acid (for example, hydrochloric acid, sulfuric acid, nitric acid, an organic acid, or the like).

In this process, the A phase is selectively removed, and the surface of the single crystal sheet is modified, whereby functional groups such as —OH, —O, and —F are introduced as terminal groups of the surface. However, in such a conventional process, the reaction control related to the functional groups, such as the introduction amount of the functional group to the surface of the single crystal sheet, is not performed, and depending on the case, there has been no concept of performing reaction control related to the functional groups.

On the other hand, as a result of intensive studies by the present inventors, it has been found that the composition and crystallite size of the inorganic compound are controlled to improve the heat resistance of the inorganic compound, by changing the amount of the MAX phase added to the removal solution, the removal condition of the A phase in the removal solution, the washing condition, the drying condition, and the like, in the above-described process. Furthermore, it has also been found that the type and amount of inevitable impurities in the inorganic compound, the shape of the inorganic compound, the amount of HF and the amount of moisture in the inorganic compound, and the like are controlled to improve the heat resistance of the inorganic compound, by changing the amount of the MAX phase added to the removal solution, the above-described conditions, and the like.

For example, as for the composition control of the inorganic compound, (b/c) can be reduced when increasing the concentration or equivalent of hydrofluoric acid contained in the removal solution. In addition, when the reaction time (removal time) is lengthened, (b/c) can be increased and ((b+c)/a) can be decreased.

In addition, the inorganic compound including M, O, F, X, and Y can be produced by using a solution containing Y as the removal solution. For example, when an acidic aqueous solution is used as the removal solution, H or the like can be introduced as Y, and when an aqueous solution containing hydrochloric acid is used as the removal solution, H and Cl can be introduced as Y In addition, as for the control of the crystallite size, the half-value width of the diffraction peak of the (110) plane obtained by X-ray diffraction analysis of the inorganic compound can be reduced by lowering the reaction temperature and lengthening the reaction time.

In addition, the kind of inevitable impurity can be change depending on the composition of the MAX phase used as a raw material. For example, when $Ti_3C_2Al$ or $Nb_2CAl$ is used, Al serves as the inevitable impurity, and when $Ti_3C_2Si$ is used, Si serves as the inevitable impurity. In addition, the amount of inevitable impurities can be controlled by, for example, the concentration of hydrofluoric acid or the number of times of washing. For example, if using a removal solution having a high hydrofluoric acid concentration, the amount of inevitable impurities can be increased, and if the number of times of washing is increased, the amount of inevitable impurities can be reduced.

Furthermore, as the shape control of the inorganic compound, it is possible to reduce the thickness of the aggregate of the inorganic compound, that is, the thickness of the layer of the inorganic compound, when increasing the hydrofluoric acid concentration in the removal solution from several percent to about 50%. In addition, when the temperature of the removal solution is raised, the thickness of the layer of the inorganic compound can be reduced.

Moreover, the amount of HF in the inorganic compound can be controlled by the number of times of washing and the washing method. For example, if the number of times of washing is increased, the amount of HF can be reduced.

In addition, the amount of moisture in the inorganic compound can be controlled according to the temperature and the pressure at the drying. For example, if the drying temperature is raised, the moisture amount can be reduced.

Furthermore, also for a dispersion containing the inorganic compound and a film containing the inorganic compound, high heat resistance, which is the effect of the inorganic compound described above, is maintained.

For example, a dispersion containing the inorganic compound can be produced by adding the inorganic compound to a solution serving as a dispersion medium and stirring the solution. In addition, various additives may be included in the dispersion to an extent such that the effect of heat resistance of the inorganic compound is not reduced.

In addition, a film containing the inorganic compound can be produced by applying the above dispersion to a substrate and removing the solvent by evaporation or the like. In addition, a film containing the inorganic compound may be produced by filling the above-described powdered inorganic compound into a mold, and then pressure molding. Thereafter, the film may be subjected to heat treatment such as calcining. In addition, the film may include various additives to an extent such that the effect of heat resistance of the inorganic compound is not reduced.

According to the first embodiment described above, the heat resistance of the inorganic compound can be increased by controlling the composition and crystallite size of the inorganic compound.

Second Embodiment

An inorganic compound according to a second embodiment includes M, O, and F, in which M is one or more kinds of transition metal elements, (b/c) is 1.50 or less when defining the molar ratio of O as "b" and defining the molar ratio of F as "c", and the half-value width of the diffraction peak of the (110) plane obtained by X-ray diffraction analysis is 0.450 or more.

As described above, the inorganic compound of the second embodiment includes M, O (oxygen), and F (fluorine).

M constituting the inorganic compound is one or more kinds of transition metal elements and is preferably an early transition metal element. For example, M may be one kind of transition metal element or may be two or more kinds of transition metal elements.

In addition, the inorganic compound may further include X in addition to M, O, and F. X constituting the inorganic compound includes at least C among C (carbon) and N (nitrogen). That is, X is either only C, or C and N.

When the inorganic compound includes M, O, F, and X, M is preferably Ti (titanium) and X is preferably C, from the viewpoint of improving the generation of methane and hydrogen at a low temperature of the inorganic compound.

In addition, the inorganic compound may further include X and Y in addition to M, O, and F. Y constituting the inorganic compound is one or more kinds of elements selected from the group consisting of H (hydrogen), an alkali metal element, an alkaline earth metal element, a chalcogen element excluding oxygen, and a halogen element excluding fluorine. For example, Y may be one kind of alkali metal element or may be one kind of alkali metal element and one kind of alkaline earth metal element. Y is preferably one or more kinds of elements selected from the group consisting of H, Li, Na, K, Be, Mg, Ca, Sr, Ba, Ra, S, Se, Te, Cl, Br and I, more preferably one or more kinds of elements selected from the group consisting of H, Li, Na, K, Mg, Ca, S, Se, Cl and Br, and still more preferably one or more kinds of elements selected from the group consisting of H, Li, Na and Cl.

When the inorganic compound includes M, O, F, X, and Y, M is preferably Ti and X is preferably C from the viewpoint of improving the generation of methane and hydrogen at a low temperature of the inorganic compound.

In addition, the inorganic compound preferably further includes one or more kinds of elements selected from the group consisting of Al, Si, Ga, P, S, Ge, As, Cd, In, Sn, Tl, and Pb (hereinafter also referred to as additive elements), and the ratio (Wi/Wm) of the total molar amount Wi of the additive elements relative to the total molar amount Wm of M is preferably 0.03 or more and 0.50 or less.

When the lower limit of the above ratio (Wi/Wm) is 0.03 or more, since distortion of the crystal structure of the inorganic compound occurs to increase the activity, the generated amounts of methane and hydrogen at a low temperature increase. Therefore, the lower limit of the ratio (Wi/Wm) is preferably 0.03 or more, more preferably 0.05 or more, and still more preferably 0.07 or more.

In addition, when the ratio (Wi/Wm) is more than 0.50, a stable new crystal is formed by the additive element, and therefore, when the upper limit of the above ratio (Wi/Wm) is 0.50 or less, methane and hydrogen are likely to be generated at a low temperature. Therefore, the upper limit of the ratio (Wi/Wm) is preferably 0.50 or less, more preferably 0.20 or less, and still more preferably 0.10 or less.

In addition, the inorganic compound may include an element other than the above-mentioned elements to an extent such that the effect of improving the generation of methane and hydrogen at a low temperature of the inorganic compound is not reduced.

In addition, the inorganic compound is preferably a layered inorganic compound (hereinafter also referred to as a layered compound), and thereamong, is more preferably a MXene. The layered inorganic compound is an inorganic compound in which primary particles or secondary particles of the inorganic compound have a sheet shape.

Suitable layered compounds include clay minerals such as smectites, magadiite, kanemite, talc and kaolinite; niobates such as potassium niobate and lithium niobate; titanates such as potassium titanate and lithium titanate; metal phosphates; layered hydroxides such as hydrotalcite; metal chalcogenides such as $MoS_2$, $WS_2$, $TaS_2$ and $NbS_2$; MXenes and MAX phases.

In addition, MXene is an inorganic compound generally represented by the compositional formula $M_{n+1}X_n$ (n is an integer of 1 to 4) and having a part or all of a crystal structure in which M atoms and X atoms are arranged in a layered manner, and FIGS. 1 to 4 are exemplified thereas, for example. FIG. 1 is a schematic diagram showing an example of the crystal structure of a $M_3X_2$ MXene. It has a structure in which layers of M atoms and layers of X atoms are alternately arranged and has surface functional group atoms on the outermost surface. FIG. 2 is a schematic diagram showing an example of the crystal structure of a $M_2X$ MXene. Although the number of layers is different from that of a $M_3X_2$ MXene, a $M_2X$ MXene also has a similar structure. FIG. 3 is a schematic diagram showing an example of a crystal structure of a MXene having a plurality of kinds of M elements and a plurality of kinds of X elements. FIG. 4 is a schematic diagram showing an example of a crystal structure of a MXene having a plurality of kinds of surface functional group atoms.

In addition, the MAX phase is an inorganic compound represented by the compositional formula $M_{n+1}AX_n$. For example, n is an integer from 1 to 4.

In the case of the inorganic compound according to the second embodiment being a MXene including M, O, F, and X, the MXene is represented by the following formula (3) when defining the molar ratio of M included in the inorganic compound as "a", the molar ratio of O as "b", the molar ratio of F as "c", and the molar ratio of X as "d". When X is composed of C and N, the molar ratio of C is represented by d1, and the molar ratio of N is represented by d2. The sum of d1 and d2 (d1+d2) is d.

$$M_aX_dO_bF_e \qquad \text{Formula (3)}$$

As the MXenes represented by the formula (3), $Ti_aC_dO_bF_e$, $Ti_aN_dO_bF_c$, $Ti_aC_{d1}N_{d2}O_bF_c$, $V_aC_dO_bF_c$, $V_aN_dO_bF_c$, $V_aC_{d1}N_{d2}O_bF_c$, $Nb_aC_dO_bF_c$, $Nb_aN_dO_bF_c$, $Nb_aC_{d1}N_{d2}O_bF_c$, $MO_aC_dO_bF_c$, $MO_aN_dO_bF_c$, $MO_aC_{d1}N_{d2}O_bF_c$, $Sc_aC_dO_bF_c$, $Sc_aN_dO_bF_c$, $Sc_aC_{d1}N_{d2}O_bF_c$, $Cr_aC_dO_bF_c$, $Cr_aN_dO_bF_c$, $Cr_aC_{d1}N_{d2}O_bF_c$, $Zr_aC_dO_bF_c$, $Zr_aN_dO_bF_c$, $Zr_aC_{d1}N_{d2}O_bF_c$, $Hf_aC_dO_bF_c$, $Hf_aN_dO_bF_c$, $Hf_aC_{d1}N_{d2}O_bF_c$, $Ta_aC_dO_bF_c$, $Ta_aN_dO_bF_e$ and $Ta_aC_{d1}N_{d2}O_bF_c$ are preferable due to their excellent ability to generate methane and hydrogen at a low temperature, and thereamong, $Ti_aC_dO_bF_e$, $Ti_aN_dO_bF_c$, $Ti_aC_{d1}N_{d2}O_bF_c$, $V_aC_dO_bF_c$, $V_aN_dO_bF_c$, $V_aC_{d1}N_{d2}O_bF_c$, $Nb_aC_dO_bF_c$, $Nb_aN_dO_bF_c$, $Nb_aC_{d1}N_{d2}O_bF_c$, $MO_aC_dO_bF_c$, $Mo_aN_dO_bF_c$, $MO_aC_{d1}N_{d2}O_bF_c$, $Cr_aC_dO_bF_c$, $Cr_aN_dO_bF_c$, $Cr_aC_{d1}N_{d2}O_bF_c$, $Ta_aC_dO_bF_c$, $Ta_aN_dO_bF_e$ and $Ta_aC_{d1}N_{d2}O_bF_c$ are more preferable due to their high methane and hydrogen generating activity, and thereamong, $Ti_aC_{d1}N_{d2}O_bF_c$, $V_aC_dO_bF_c$, $V_aN_dO_bF_c$, $V_aC_{d1}N_{d2}O_bF_c$, $Nb_aC_dO_bF_c$, $Nb_aN_dO_bF_c$ and $Nb_aC_{d1}N_{d2}O_bF_c$ are more preferable due to their ease of synthesis.

In addition, when the inorganic compound is a MXene including M, O, F, X, and Y, the MXene is represented by the following formula (4), when defining the molar ratio of M included in the inorganic compound as "a", the molar ratio of O as "b", the molar ratio of F as "c", the molar ratio of X as "d", and the molar ratio of Y as "e". When Y is composed of n kinds of elements of Y1 to Yn (n is an integer of 1 or more), the molar ratios of the respective elements of Y are represented by e1 to en, respectively. The sum of e1 to en (e1+ . . . +en) is e.

$$M_aX_dO_bF_cY_e \qquad \text{Formula (4)}$$

From the viewpoint of improving the generation of methane and hydrogen at a low temperature of the inorganic compound, as the MXene represented by the formula (4), Y preferably includes one or more kinds of elements selected from the group consisting of H, Li, Na, K, Be, Mg, Ca, Sr, Ba, Ra, S, Se, Te, Cl, Br and I, more preferably includes one or more kinds of elements selected from the group consisting of H, Li, Na, K, Mg, Ca, S, Se, Cl and Br, and still more preferably includes one or more kinds of elements selected from the group consisting of H, Li, Na and Cl. Specific examples of the MXene represented by the formula (4) include $Ti_aC_dO_bF_cH_e$, $Ti_aN_dO_bF_cH_e$, $Ti_aC_{d1}N_{d2}O_bF_cH_e$, $Ti_aC_dO_bF_cH_{e1}Li_{e2}$, $Ti_aN_dO_bF_cH_{e1}Li_{e2}$, $Ti_aC_{d1}N_{d2}O_bF_cH_{e1}Li_{e2}$, $Ti_aC_dO_bF_cH_{e1}Cl_{e2}$, $Ti_aN_dO_bF_cH_{e1}Cl_{e2}$ and $Ti_aC_{d1}N_{d2}O_bF_cH_{e1}Cl_{e2}$.

For the inorganic compound, when defining the molar ratio of 0 included in the inorganic compound as "b" and the molar ratio of F as "c", (b/c) is 1.50 or less. When (b/c) is 1.50 or less, the ability to generate methane and hydrogen at a low temperature is high. Therefore, (b/c) is 1.50 or less, preferably 1.00 or less, more preferably 0.70 or less, and still more preferably 0.50 or less.

In addition, from the viewpoint of the synthesis of the inorganic compound being easy, the lower limit of (b/c) is preferably 0.01 or more, more preferably 0.05 or more, still more preferably 0.10 or more, and particularly preferably 0.40 or more.

In addition, when defining the molar ratio of M included in the inorganic compound as "a", ((b+c)/a) is preferably 0.50 or more. When ((b+c)/a) is 0.50 or more, the generation of methane and hydrogen of the inorganic compound at a low temperature can be further improved. Therefore, ((b+c)/a) is preferably 0.50 or more, more preferably 0.90 or more, still more preferably 1.30 or more, and is preferably as large as possible.

In addition, the upper limit of ((b+c)/a) is preferably, for example, 5.00 or less, and more preferably 3.00 or less, in order to reduce the amount of products such as water other than methane and hydrogen.

The molar ratio a of M, the molar ratio b of 0, and the molar ratio c of F contained in the inorganic compound can be measured by SEM-EDX.

In addition, the half-value width of the diffraction peak of the (110) plane obtained by X-ray diffraction analysis of the inorganic compound (hereinafter also simply referred to as half-value width) is 0.450 or more, preferably 0.50° or more, more preferably 0.600 or more, and is preferably as large as possible. When the half-value width is 0.450 or more, the generation of methane and hydrogen of the inorganic compound at a low temperature can be improved, and the generation can be improved with larger half-value width. In addition, the upper limit of the half-value width is, for example, 1.000 or less.

The X-ray diffraction analysis of the inorganic compound is performed as follows. Using an X-ray diffractometer, the sample holder is filled with a powdered inorganic compound, the X-ray diffraction intensity between, for example, 3° and 80° is measured by the θ-2θ method, and the background value, which is noise, is subtracted from the peak intensity to obtain the diffraction peak of the (110) plane. Based on the obtained diffraction peak of the (110) plane, the half-value width is calculated. At this time, a characteristic X-ray (wavelength: 0.154 nm) of CuKα is used as the X-ray.

In addition, the inorganic compound is preferably in a layered form, and the thickness of the layer is preferably 0.20 μm or less, more preferably 0.18 μm or less, still more preferably 0.12 μm or less, and is preferably as small as possible. When the thickness of the layer of the inorganic compound is 0.20 μm or less, since the specific surface area of the inorganic compound is increased, the number of active points is increased, so that the generation of methane and hydrogen of the inorganic compound can be further improved, and the generation can be improved with smaller thickness of the layer. In addition, the lower limit of the thickness of the film is, for example, 0.05 μm or more.

The thickness of the layer of the inorganic compound is not the thickness of a single crystal sheet (sheet-shaped single crystal) of the inorganic compound, but rather the thickness of a sheet-shaped aggregate obtained by stacking a plurality of single crystal sheets of the inorganic compound via a gap of approximately 0.05 μm or less. The shape of the inorganic compound and the thickness of the layer of the inorganic compound are measured by observing the powdered inorganic compound with a scanning electron microscope (SEM).

In addition, in the case where hydrogen fluoride (HF) is contained in the inorganic compound, the lower limit for the weight ratio of HF in the inorganic compound relative to the total amount of the inorganic compound (hereinafter also simply referred to as the weight ratio of HF) is preferably 1 ppt or more, more preferably 1 ppb or more, and even more preferably 1 ppm or more, and the upper limit of the weight ratio of HF is preferably 100 ppm or less, more preferably 50 ppm or less, and even more preferably 20 ppm or less. When the weight ratio of HF is 1 ppt or more, the generation of methane and hydrogen of the inorganic compound at a low temperature can be further improved. In addition, when the weight ratio of HF is 100 ppm or less, safety of the inorganic compound against toxicity of HF is sufficient.

The weight ratio of HF can be determined by mixing the inorganic compound and an organic solvent that can dissolve HF, and stirring the mixture for 24 hours, then measuring the F ion concentration in the organic solvent by ion chromatography to quantify the HF weight extracted in the organic solvent and dividing the HF weight by the weight of the inorganic compound.

In addition, in the case where moisture is contained in the inorganic compound, the lower limit for the weight ratio of moisture in the inorganic compound relative to the total amount of the inorganic compound (hereinafter also simply referred to as the weight ratio of moisture) is preferably 1 ppm or more, more preferably 10 ppm or more, and even more preferably 50 ppm or more, and the upper limit of the weight ratio of moisture is preferably 1.0% or less, more preferably 0.7% or less, and even more preferably 0.5% or less. When the weight ratio of moisture is 1 ppm or more, the amounts of methane and hydrogen generated at a low temperature increase. In addition, when the weight ratio of moisture is 1.0% or less, gasses other than methane and hydrogen such as water can be prevented from being mixed into the product gas.

The weight ratio of moisture can be determined by mixing the inorganic compound and an organic solvent miscible with water, stirring the mixture for 24 hours, quantifying the weight of moisture in the organic solvent by a Karl Fischer moisture meter or the like, and dividing the weight of moisture by the weight of the inorganic compound.

Since such an inorganic compound of the second embodiment is excellent in the generation of methane and hydrogen at a low temperature, a high-temperature environment as is conventional way becomes unnecessary.

Next, an example of a method for producing an inorganic compound according to the second embodiment will be described.

For example, a MAX phase (max phase) is added to a solution for selectively removing the A phase (hereinafter also referred to as a removal solution), and the A phase of the MAX phase is selectively removed, thereby generating aggregates in which a nano-sized single crystal sheet mainly composed of M and X and a plurality of the single crystal sheets are stacked. Thereafter, the aggregates generated in the solution are washed and dried to obtain powdery aggregates. This process itself is a common method of producing conventional MXenes. Here, A is a group 13 element or a group 14 element of the periodic table. The removal solution is preferably hydrofluoric acid which is a hydrogen fluoride (HF) solution. In addition, the removal solution may be a mixed solution obtained by mixing hydrofluoric acid with another acid (for example, hydrochloric acid, sulfuric acid, nitric acid, an organic acid, or the like).

In this process, the A phase is selectively removed, and the surface of the single crystal sheet is modified, whereby functional groups such as —OH, —O, and —F are introduced as terminal groups of the surface. However, in such a conventional process, the reaction control related to the functional groups, such as the introduction amount of the functional group to the surface of the single crystal sheet, is not performed, and depending on the case, there has been no concept of performing reaction control related to the functional groups.

On the other hand, as a result of intensive studies by the present inventors, it has been found that the composition and crystallite size of the inorganic compound are controlled to enhance the generation of methane and hydrogen of the inorganic compound at a low temperature, by changing the amount of the MAX phase added to the removal solution, the removal condition of the A phase in the removal solution, the washing condition, the drying condition, and the like, in the above-described process. Furthermore, it has also been found that the type and the amount of the additive element in the inorganic compound, the shape of the inorganic compound, the amount of HF and the amount of moisture in the inorganic compound, and the like are controlled to enhance the generation of methane and hydrogen of the inorganic compound at a low temperature, by changing the amount of the MAX phase added to the removal solution, the above-described conditions, and the like.

For example, as for the composition control of the inorganic compound, (b/c) can be reduced when increasing the concentration or equivalent of hydrofluoric acid contained in the removal solution. In addition, when the reaction time (removal time) is lengthened, (b/c) can be increased and ((b+c)/a) can be decreased.

In addition, the inorganic compound including M, O, F, X, and Y can be produced by using a solution containing Y as the removal solution. For example, when an acidic aqueous solution is used as the removal solution, H or the like can be introduced as Y, and when an aqueous solution containing hydrochloric acid is used as the removal solution, H and Cl can be introduced as Y In addition, as for the control of the crystallite size, the half-width value of the diffraction peak of the (110) plane obtained by X-ray diffraction analysis of the inorganic compound can be increased by raising the reaction temperature and shortening the reaction time.

In addition, the kind of the additive element can be changed depending on the composition of the MAX phase used as the raw material. For example, when $Ti_3C_2Al$ is used, Al serves as the additive element, and when $Ti_3C_2Si$ is used, Si serves as the additive element. In addition, the amount of the additive element can be controlled by, for example, the concentration of hydrofluoric acid or the number of times of washing. For example, if using a removal solution having a high hydrofluoric acid concentration, the amount of additive element can be increased, and if the number of times of washing is increased, the amount of additive element can be reduced.

Furthermore, as the shape control of the inorganic compound, it is possible to reduce the thickness of the aggregate of the inorganic compound, that is, the thickness of the layer of the inorganic compound, when increasing the hydrofluoric acid concentration in the removal solution from several percent to about 50%. In addition, when the temperature of the removal solution is raised, the thickness of the layer of the inorganic compound can be reduced.

Moreover, the amount of HF in the inorganic compound can be controlled by the number of times of washing and the washing method. For example, if the number of times of washing is increased, the amount of HF can be reduced.

In addition, the amount of moisture in the inorganic compound can be controlled according to the temperature and the pressure at the drying. For example, if the drying temperature is raised, the moisture amount can be reduced.

Furthermore, also for a dispersion containing the inorganic compound and a film containing the inorganic compound, an improvement of the generation of methane and hydrogen at a low temperature, which is the effect of the inorganic compound described above, is maintained.

For example, a dispersion containing the inorganic compound can be produced by adding the inorganic compound to a solution serving as a dispersion medium and stirring the solution. In addition, various additives may be included in the dispersion to an extent such that the effect of improving the generation of methane and hydrogen of the inorganic compound at a low temperature is not reduced.

In addition, a film containing the inorganic compound can be produced by applying the above dispersion to a substrate and removing the solvent by evaporation or the like. In addition, a film containing the inorganic compound may be produced by filling the above-described powdered inorganic compound into a mold, and then pressure molding. Thereafter, the film may be subjected to heat treatment such as calcining. In addition, the film may include various additives to an extent such that the effect of improving the generation of methane and hydrogen at a low temperature of the inorganic compound is not reduced.

Next, a method for producing methane and hydrogen will be described.

The method for producing methane and hydrogen includes a heating step of heating the inorganic compound according to the second embodiment. By heating the inorganic compound of the second embodiment in the heating step, methane and hydrogen can be produced. The temperature at which the inorganic compound is heated in the heating step is, for example, lower than the thermal decomposition temperature of the conventionally reported MXenes.

Another method for producing methane and hydrogen includes a contacting step of bringing the inorganic compound of the second embodiment into contact with an alcohol or water. Methane and hydrogen can be produced by bringing the inorganic compound of the second embodiment into contact with an alcohol or water in the contacting step. Unlike the above-described method for producing methane and hydrogen, this method for producing methane and hydrogen does not require heat treatment.

According to the second embodiment described above, by controlling the composition and crystallite size of the inorganic compound, the generation of methane and hydrogen of the inorganic compound at a low temperature can be enhanced.

Although embodiments have been described above, the present invention is not to be limited to the above embodiments, and various modifications can be made within the scope of the present disclosure, including all aspects included in the concept of the present disclosure and scope of the claims.

EXAMPLES

Next, examples and comparative examples will be described; however, the present disclosure is not to be limited to these examples.

Example 1

To 100 g of a 7.5% HF aqueous solution, 5 g of $Ti_3C_2Al$ powder was added while stirring. After the $Ti_3C_2Al$ was added, the solution temperature was raised to 35° C. and stirred for 24 hours. Thereafter, the reaction solution was filtered, and the filtered product was repeatedly washed with distilled water until the filtrate became neutral. The filtered product after washing was dried at 150° C. for 24 hours under a nitrogen atmosphere to obtain the MXene that is the inorganic compound of Example 1. Each condition is shown in Table 1.

Example 2

To 30 g of a 25.0% HF aqueous solution, 5 g of $Ti_3C_2Al$ powder was added while stirring. After the $Ti_3C_2Al$ powder was added, the solution temperature was raised to 45° C. and stirred for 24 hours. Thereafter, the reaction solution was filtered, and the filtered product was repeatedly washed with distilled water until the filtrate became neutral. The filtered product after washing was dried at 150° C. for 24 hours under a nitrogen atmosphere to obtain the MXene that is the inorganic compound of Example 2.

Comparative Example 1

To 50 g of a 50.0% HF aqueous solution, 5 g of $Ti_3C_2Al$ powder was added while stirring. After the $Ti_3C_2Al$ powder was added, the solution temperature was raised to 60° C. and stirred for 3 hours. Thereafter, the reaction solution was filtered, and the filtered product was repeatedly washed with distilled water until the filtrate became neutral. The filtered product after washing was dried at 150° C. for 24 hours under a nitrogen atmosphere to obtain the MXene that is the inorganic compound of Comparative Example 1.

Example 3

To 100 g of a 10.0% HF aqueous solution, 5 g of $Ti_3C_2Al$ powder was added while stirring. After the $Ti_3C_2Al$ powder was added, the mixture was stirred at room temperature for 24 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Example 3.

Examples 4 to 8, and Comparative Examples 2 to 4

MXenes which are the inorganic compounds of Examples 4 to 8 and Comparative Examples 2 to 4 were obtained in the same manner as in Example 3, except for changing to the conditions shown in Table 1.

Example 9

To a removal solution obtained by mixing 32.61 g of a 46% HF aqueous solution, 120 g of 37% hydrochloric acid and 47.39 g of distilled water, 10 g of $Ti_3C_2Al$ powder was added while stirring. After the $Ti_3C_2Al$ powder was added, the solution temperature was raised to 35° C. and stirred for 24 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Example 9.

Example 10

To 100 g of a 7.5% HF aqueous solution, 5 g of $Ti_3C_2Al$ powder was added while stirring. After the $Ti_3C_2Al$ powder was added, the solution temperature was raised to 35° C. and stirred for 24 hours. Thereafter, the reaction solution was filtered, and the filtered product was repeatedly washed with distilled water until the filtrate became neutral. The filtered product after washing was dried using a tube furnace at 150°

C. for 24 hours under a nitrogen atmosphere, and then calcined at 400° C. for 1 hour under a nitrogen atmosphere to obtain the MXene that is the inorganic compound of Example 10.

Comparative Example 5

To 3 g of MXene of Example 1, 177 g of a 15% aqueous solution of tetramethylammonium hydroxide was added, and the mixture was stirred for 24 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Comparative Example 5.

Comparative Example 6

To 3 g of MXene of Comparative Example 1, 177 g of a 15% aqueous solution of tetramethylammonium hydroxide was added, and the mixture was stirred for 24 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Comparative Example 6.

Example 11

To 100 g of 50% HF aqueous solution, 10 g of $Nb_2CAl$ powder was added while stirring. After the $Nb_2CAl$ powder was added, the mixture was stirred at room temperature for 96 hours. Thereafter, the reaction solution was filtered, and the filtered product was repeatedly washed with distilled water until the filtrate became neutral. The filtered product after washing was dried at 200° C. for 24 hours under a nitrogen atmosphere to obtain the MXene that is the inorganic compound of Example 11.

TABLE 1

| | Inorganic compound | HF concentration (%) | Removal solution amount (g) | Reaction time (h) | Reaction temperature (° C.) | Drying atmosphere | Drying temperature (° C.) |
|---|---|---|---|---|---|---|---|
| Example 1 | MXene | 7.5 | 100 | 24 | 35 | Nitrogen | 150 |
| Example 2 | MXene | 25.0 | 30 | 24 | 45 | Nitrogen | 150 |
| Example 3 | Mxene | 10.0 | 100 | 24 | Room temperature | Reduced pressure | 80 |
| Example 4 | MXene | 25.0 | 30 | 24 | 35 | Reduced pressure | 80 |
| Example 5 | MXene | 25.0 | 100 | 24 | 35 | Reduced pressure | 80 |
| Example 6 | MXene | 25.0 | 100 | 5 | 35 | Reduced pressure | 80 |
| Example 7 | MXene | 7.5 | 333 | 24 | 35 | Reduced pressure | 80 |
| Example 8 | MXene | 7.5 | 100 | 24 | 60 | Reduced pressure | 80 |
| Comparative Example 1 | MXene | 50.0 | 50 | 3 | 60 | Nitrogen | 150 |
| Comparative Example 2 | MXene | 25.0 | 30 | 5 | 70 | Reduced pressure | 80 |
| Comparative Example 3 | MXene | 25.0 | 100 | 5 | 60 | Reduced pressure | 80 |
| Comparative Example 4 | MXene | 50.0 | 50 | 24 | 60 | Reduced pressure | 80 |

[Measurement and Evaluation]

The inorganic compounds obtained in Examples 1 to 11 and Comparative Examples 1 to 6 were subject to the below measurements and evaluations. The results are shown in Table 2.

[1] Molar Ratio a of M, Molar Ratio b of O, and Molar Ratio c of F

Elemental analysis of the inorganic compound was performed by SEM-EDX measurement, and the molar ratio (at %) of each element was determined. The molar ratio of M was defined as "a", the molar ratio of O was defined as "b", and the molar ratio of F was defined as "c". The molar ratio of O was divided by the molar ratio of F to obtain (b/c), and the sum of the molar ratio of O and the molar ratio of F was divided by the molar ratio of M to obtain (b+c)/a. The SEM-EDX measurement conditions are as follows.

Apparatus: JED-2300 (JEOL Ltd.)
Acceleration voltage: 20 kV

[2] Half-Value Width of Diffraction Peak of (110) Plane

The X-ray diffraction pattern of the inorganic compound was obtained by XRD measurement, and the half-value width of the diffraction peak of the (110) plane was obtained. The XRD measurement conditions are as follows.

Apparatus: fully-automated horizontal multipurpose X-ray diffractometer, SmartLab (Rigaku Corp.)
X-ray tube bulb: Cu
X-Ray Output: 40 kV, 50 mA
Filter: Cu_Kβ
Sample Preparation Method: filled to silicon non-reflective plate

[3] Ratio (Wi/Wm)

Elemental analysis of the inorganic compound was performed by SEM-EDX measurement, and the molar ratio (at %) of each element was determined. The molar ratio of M was defined as "Wm" and the molar ratio of the inevitable impurities was defined as "Wi". The molar ratio (Wi/Wm) was determined by dividing the molar ratio of the inevitable impurities by the molar ratio of M. The SEM-EDX measurement conditions are as follows.

Apparatus: JED-2300 (JEOL Ltd.)
Acceleration voltage: 20 kV

[4] Layer Thickness Observation of the shape of the inorganic compound and the thickness measurement of the layer were performed by SEM observation. For the thickness of the layer, 20 samples of a flat particle in the image were randomly selected and the thickness thereof was measured, and the average value thereof was taken as the thickness of the layer. A TSM-7610F (JEOL Ltd.) was used for SEM measurement.

[5] Weight Ratio of HF The weight ratio of HF in the inorganic compound was calculated by mixing 10 g of acetonitrile and 1 g of the inorganic compound, stirring the mixture for 24 hours, followed by quantifying the F ion concentration in the acetonitrile by ion chromatography measurement, calculating the weight (g) of HF eluted in the acetonitrile, and dividing the weight of HF by 1 g of weight of the inorganic compound.

[6] Weight Ratio of Moisture

The weight ratio of the moisture in the inorganic compound was calculated by mixing 10 g of acetonitrile and 1 g of the inorganic compound, stirring the mixture for 24 hours, followed by quantifying the moisture amount in the acetonitrile by a Karl Fischer moisture meter, and dividing the moisture amount by 1 g of the weight of the inorganic compound.

[7] Heat Resistance

As a heat resistance evaluation of the inorganic compound, the change in weight with respect to temperature was measured by TG (thermogravimetric) measurement. The TG measurement conditions are as follows.

Apparatus: thermogravimetric apparatus TGA-50 (Shimadzu Corp.)
Sample Cell: Pt
Rate of temperature increase: 10° C./min
Temperature Range: room temperature to 1000° C.
Atmosphere: $H_e$ gas
Gas Flow Rate: 100 ml/min

TABLE 2

| | M | X | Y | Inevitable impurity | Ratio (Wi/Wm) | (b/c) | ((b + c)/a) | Half-value width (°) | Layer thickness (nm) | Weight ratio of HF (ppm) | Weight ratio of moisture (ppm) | Weight change (%) r.t. ~350° C. | Weight change (%) r.t. ~1000° C. | Weight change (%) 350~1000° C. |
|---|---|---|---|---|---|---|---|---|---|---|---|---|---|---|
| Example 1 | Ti | C | H | Al | 0.015 | 1.67 | 0.94 | 0.47 | 212 | 10 | 132 | −1.4 | −6.1 | −4.7 |
| Example 2 | Ti | C | H | Al | 0.022 | 1.44 | 1.05 | 0.43 | 151 | 10 | 301 | −3.5 | −6.4 | −2.9 |
| Example 3 | Ti | C | H | Al | 0.016 | 2.00 | 1.27 | 0.48 | 250 | 10 | 118 | −0.7 | −4.6 | −3.9 |
| Example 4 | Ti | C | H | Al | 0.027 | 1.20 | 0.82 | 0.35 | 189 | 10 | 178 | −1.3 | −7.2 | −5.9 |
| Example 5 | Ti | C | H | Al | 0.004 | 1.02 | 0.85 | 0.46 | 180 | 10 | 387 | −4.5 | −9.6 | −5.2 |
| Example 6 | Ti | C | H | Al | 0.027 | 0.79 | 1.54 | 0.50 | 175 | 10 | 401 | −5.7 | −8.9 | −3.2 |
| Example 7 | Ti | C | H | Al | 0.001 | 0.67 | 0.48 | 0.35 | 235 | 10 | 203 | −1.3 | −4.4 | −3.1 |
| Example 8 | Ti | C | H | Al | 0.006 | 1.34 | 0.69 | 0.55 | 155 | 10 | 355 | −4.1 | −10.9 | −6.8 |
| Example 9 | Ti | C | H, Cl | Al | 0.008 | 1.22 | 1.38 | 0.38 | 240 | 10 | 421 | −3.2 | −4.5 | −1.3 |
| Example 10 | Ti | C | H | Al | 0.013 | 2.23 | 0.96 | 0.47 | 212 | 10 | 107 | −0.075 | −6.73 | −6.655 |
| Example 11 | Nb | C | H | Al | 0.380 | 1.27 | 1.15 | 0.30 | 8400 | 20 | 1029 | −0.8 | −1.14 | −0.34 |
| Comparative Example 1 | Ti | C | H | Al | 0.076 | 0.47 | 1.33 | 0.67 | 82 | 10 | 3532 | −4.4 | −23.9 | −19.5 |
| Comparative Example 2 | Ti | C | H | Al | 0.077 | 0.75 | 1.52 | 0.62 | 110 | 10 | 1241 | −6.9 | −17.3 | −10.3 |
| Comparative Example 3 | Ti | C | H | Al | 0.090 | 0.58 | 1.64 | 0.62 | 103 | 10 | 879 | −5.4 | −11.2 | −5.8 |
| Comparative Example 4 | Ti | C | H | Al | 0.080 | 0.37 | 2.15 | 0.58 | 92 | 40 | 3297 | −7.7 | −24.1 | −16.4 |

TABLE 2-continued

| | M | X | Y | Inevi-table impurity | Ratio (Wi/Wm) | (b/c) | ((b + c)/a) | Half-value width (°) | Layer thick-ness (nm) | Weight ratio of HF (ppm) | Weight ratio of moisture (ppm) | Weight change (%) r.t. ~350° C. | Weight change (%) r.t. ~1000° C. | Weight change (%) 350~1000° C. |
|---|---|---|---|---|---|---|---|---|---|---|---|---|---|---|
| Comparative Example 5 | Ti | C | H | Al | Less than Al detection lower limit | 3.04 | 2.04 | 0.40 | Evaluation not possible | 1 | 539 | −9.6 | −17.2 | −7.6 |
| Comparative Example 6 | Ti | C | H | Al | Less than Al detection lower limit | 2.42 | 1.85 | 0.56 | Evaluation not possible | 2 | 761 | −10.2 | −19.2 | −9.0 |

Figure 5:
FIG. 5 is TG data of the inorganic compound in Example 1.
Figure 6:
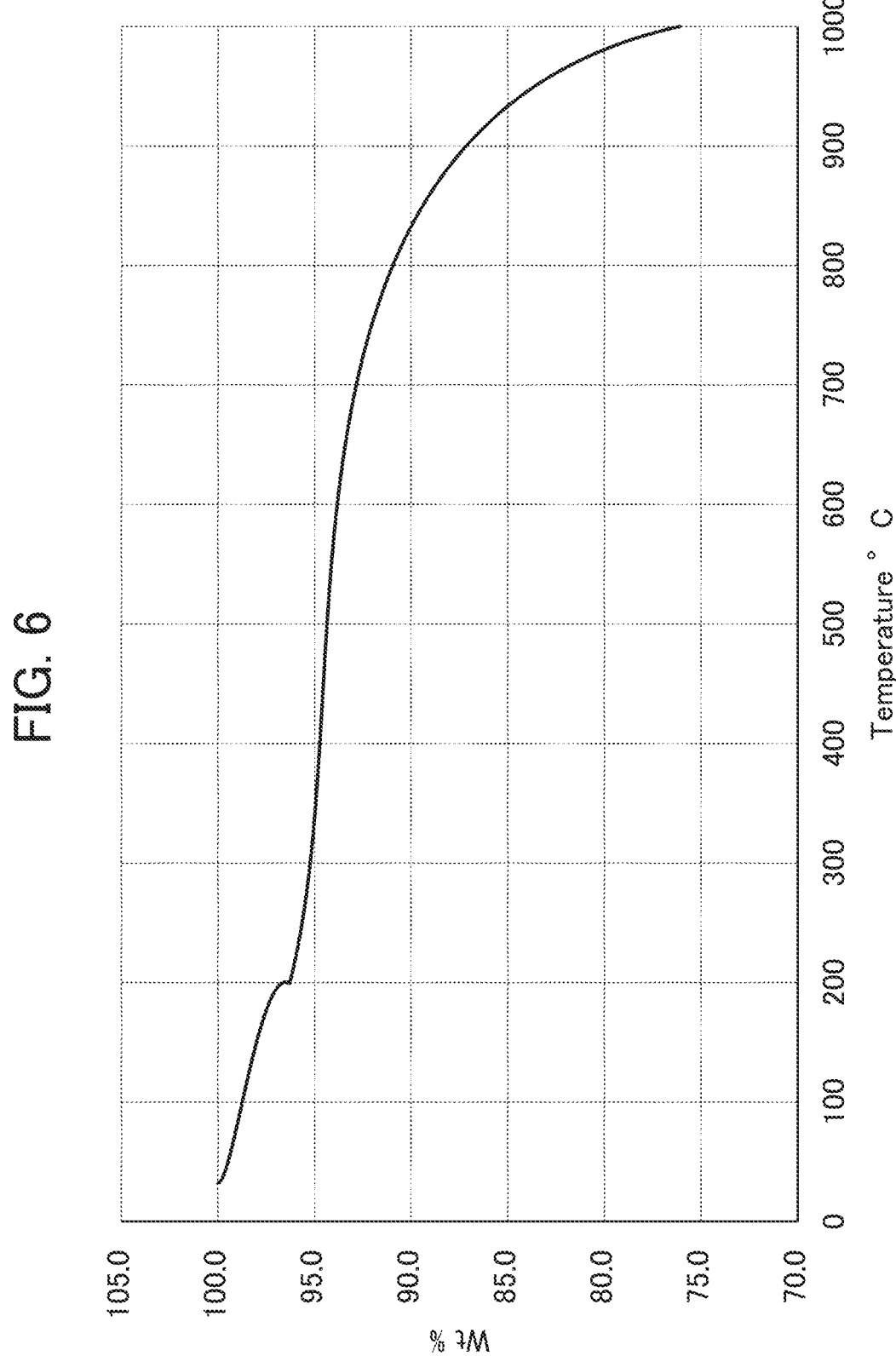
FIG. 6 is TG data of the inorganic compound in Comparative Example 1.
Figure 7:
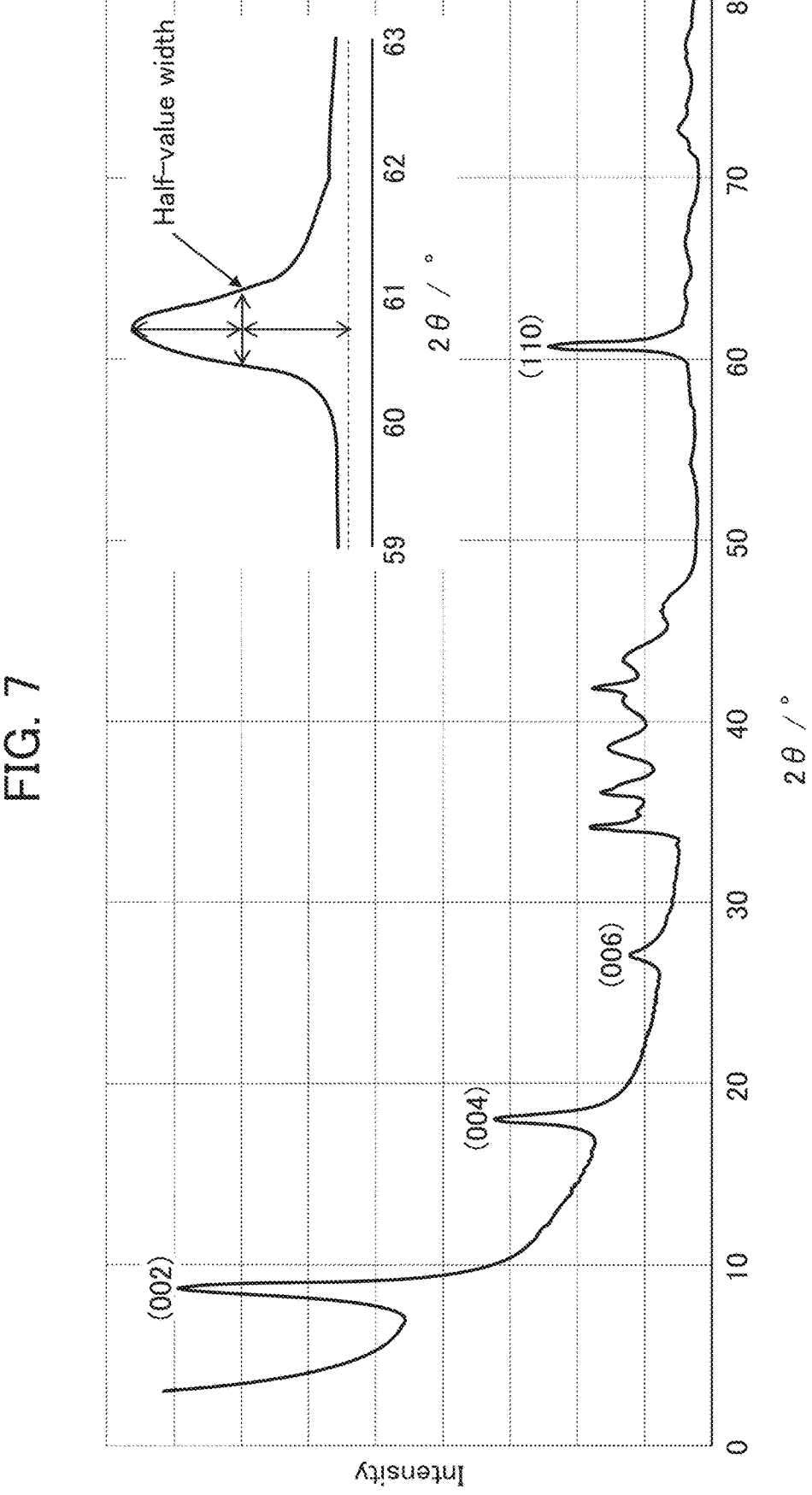
FIG. 7 is XRD data of the inorganic compound in Example 1.
Figure 8:
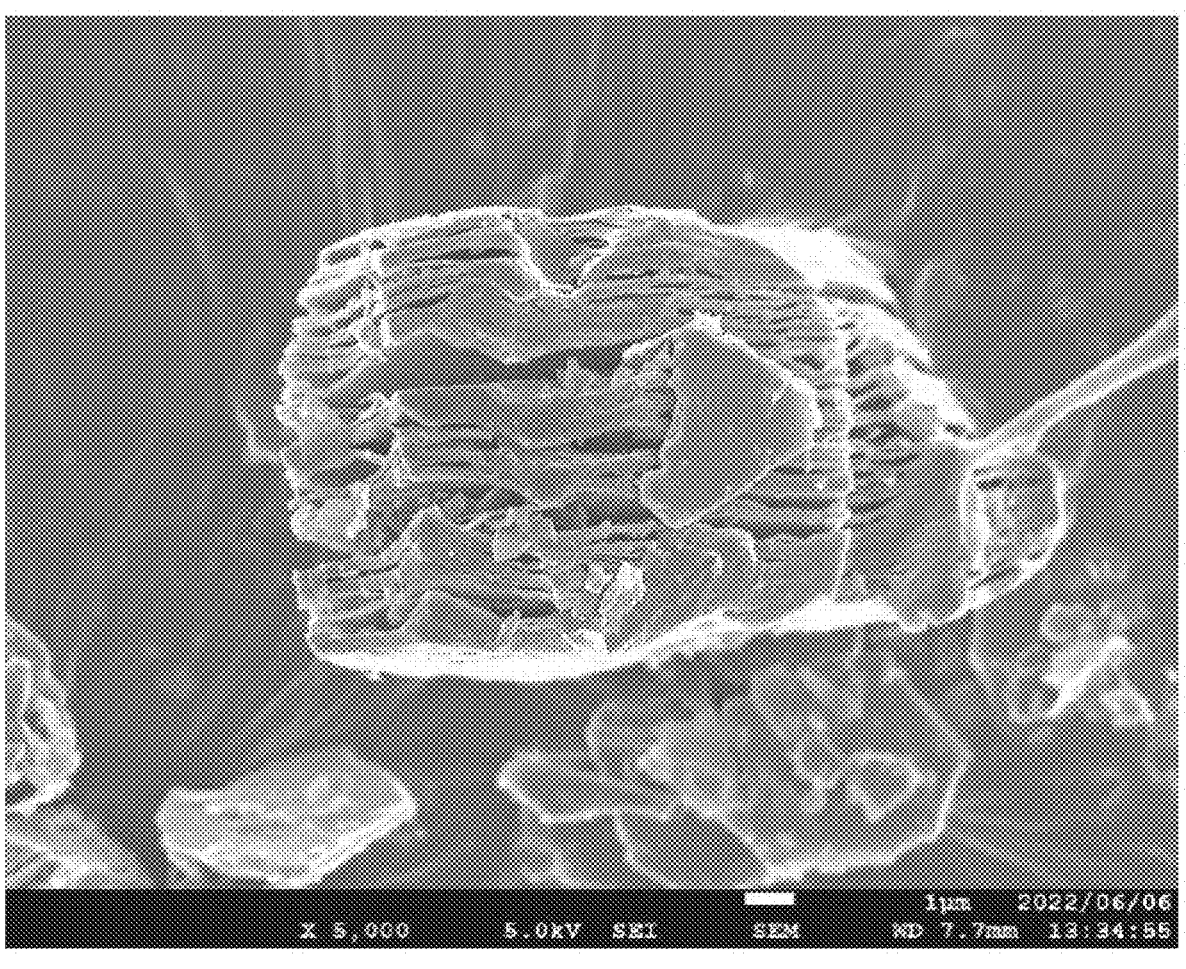
FIG. 8 is an SEM image of the inorganic compound in Example 4.
Figure 9:
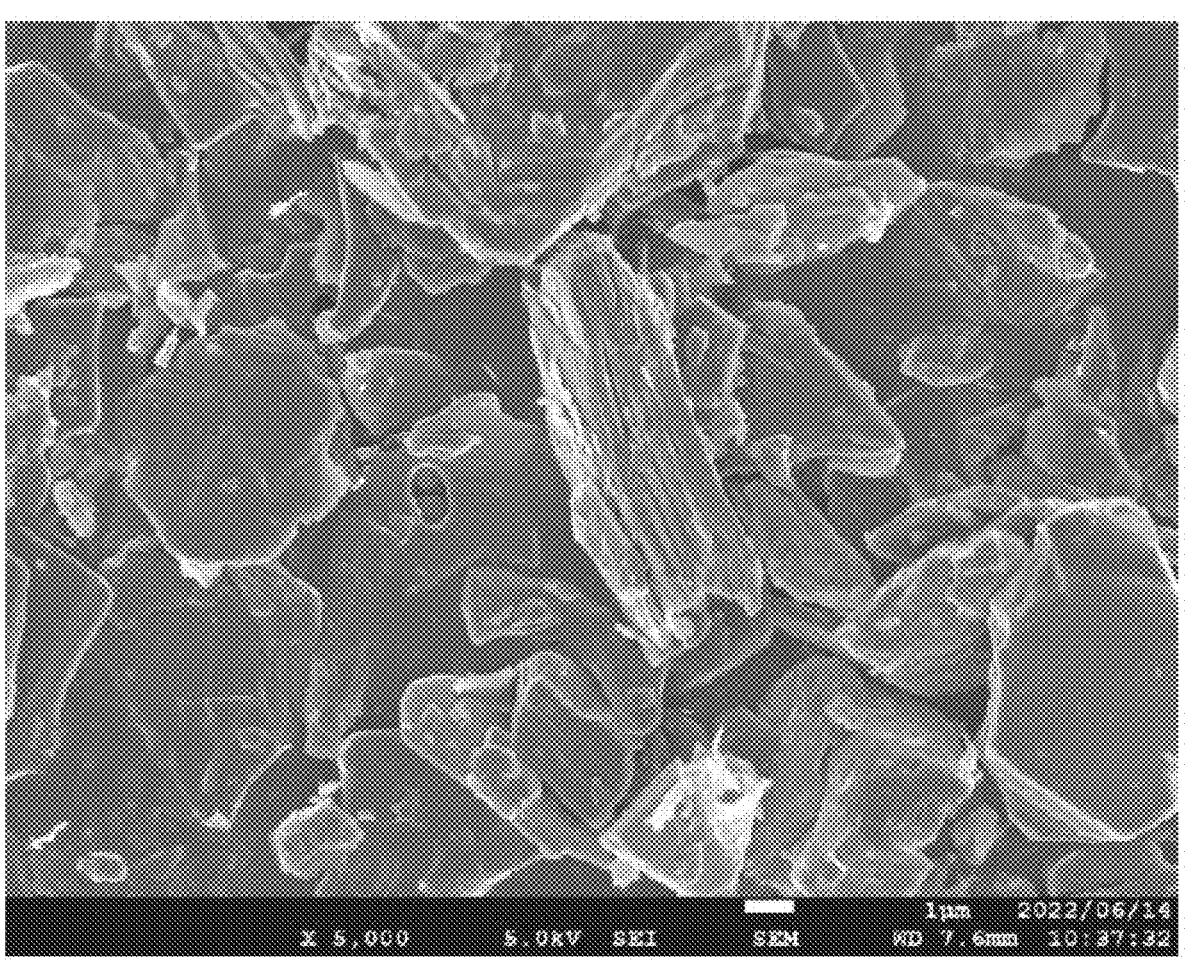
FIG. 9 is an SEM image of the inorganic compound in Example 7.
Figure 10:
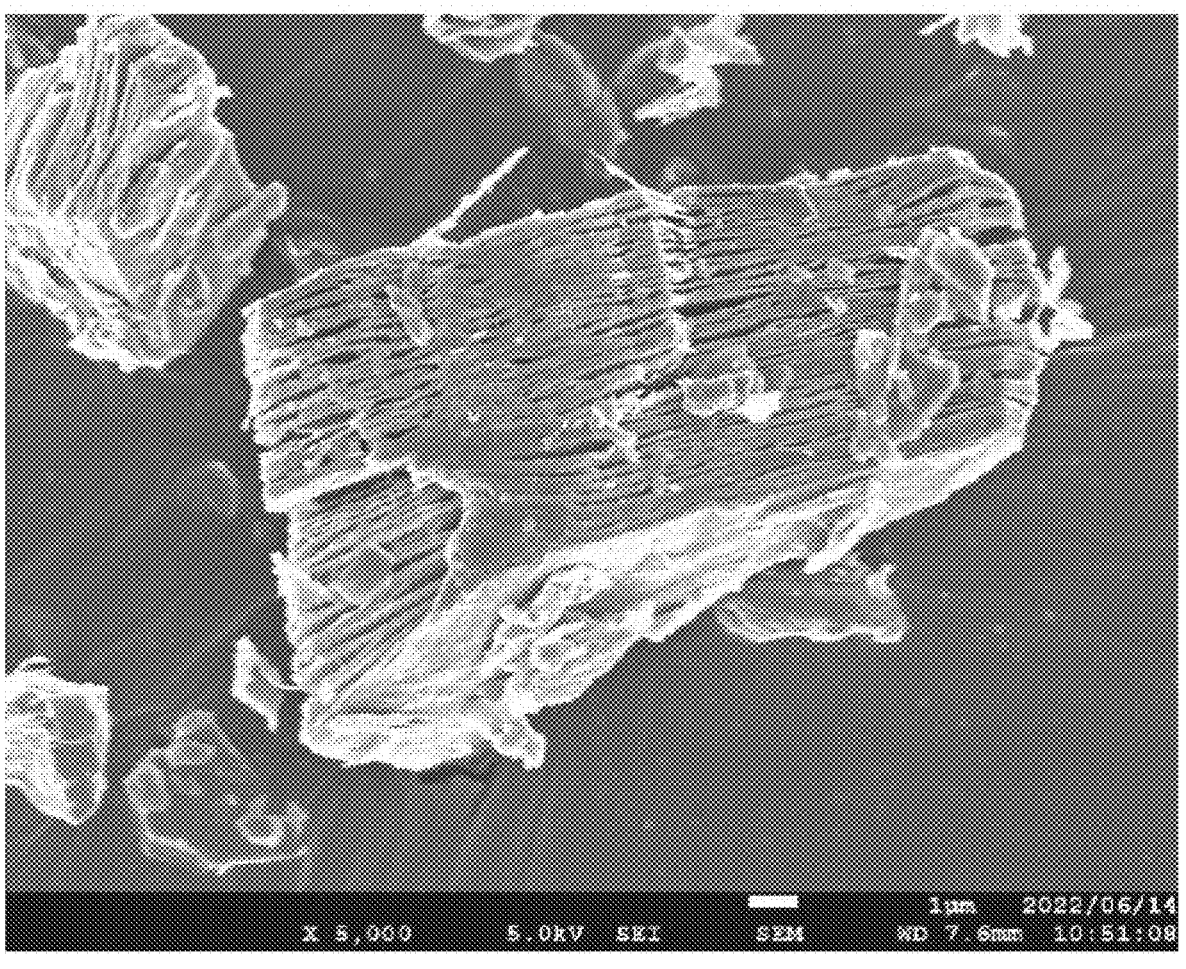
FIG. 10 is an SEM image of the inorganic compound in Example 10.
Figure 11:
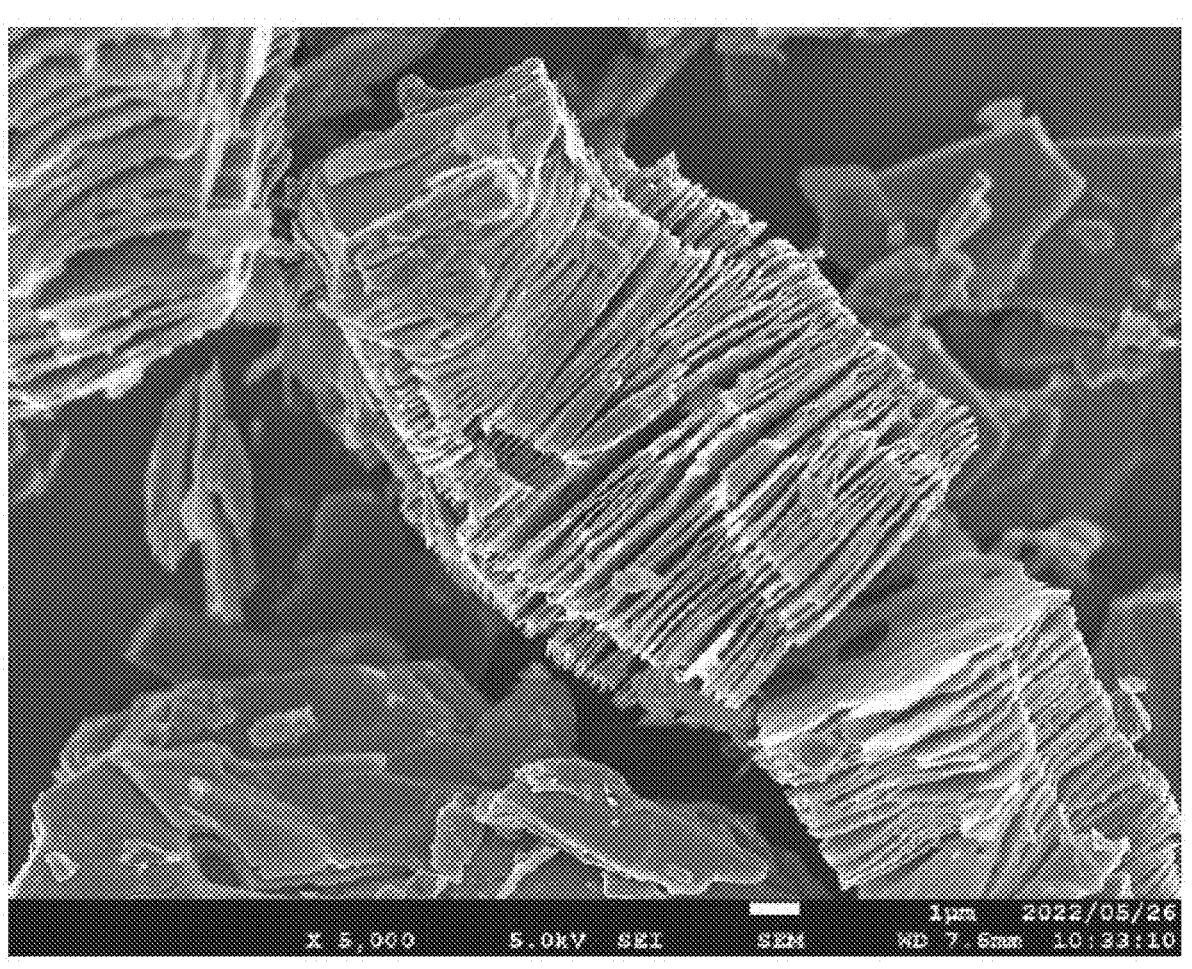
FIG. 11 is an SEM image of the inorganic compound in Comparative Example 1.
Figure 12:
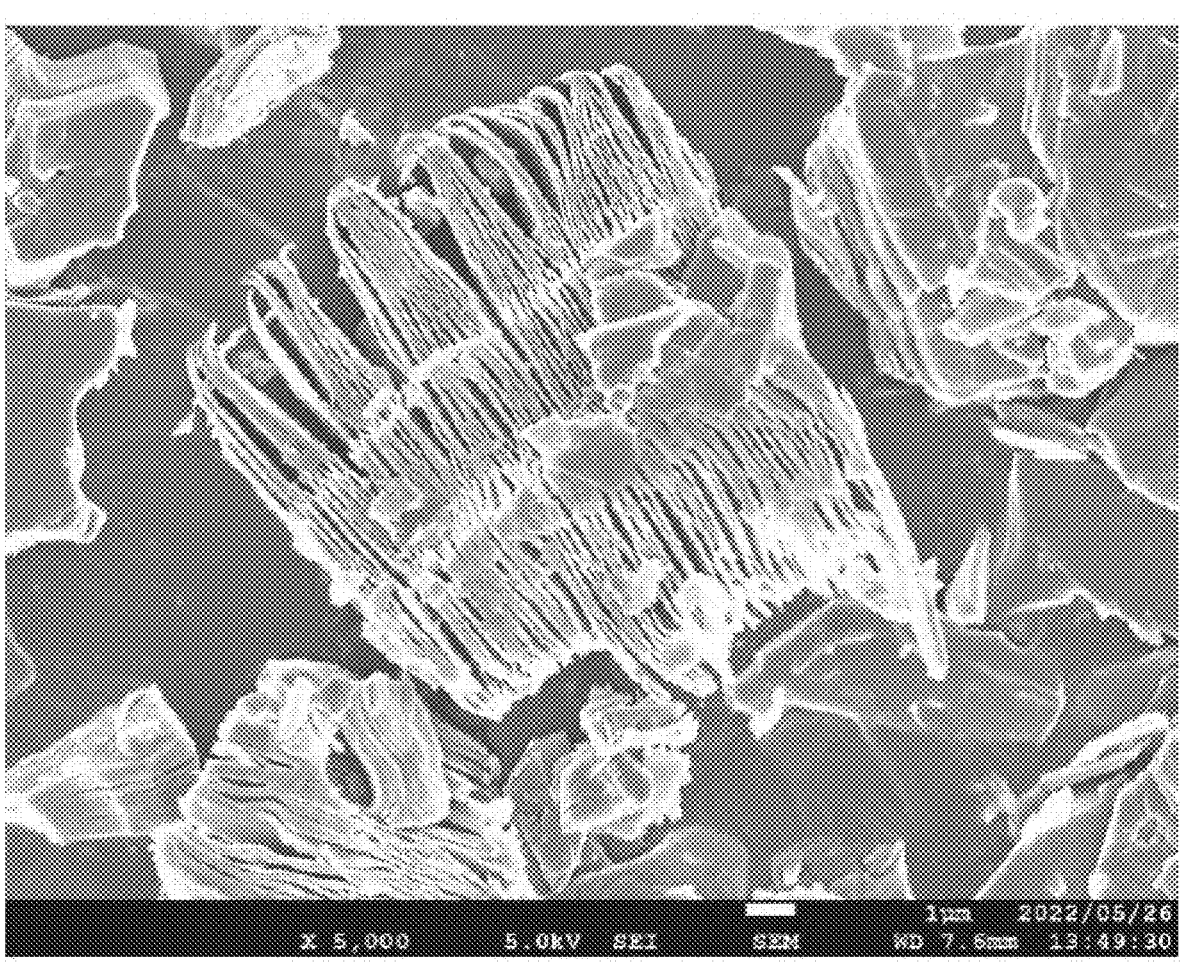
FIG. 12 is an SEM image of the inorganic compound in Comparative Example 2.
Figure 13:
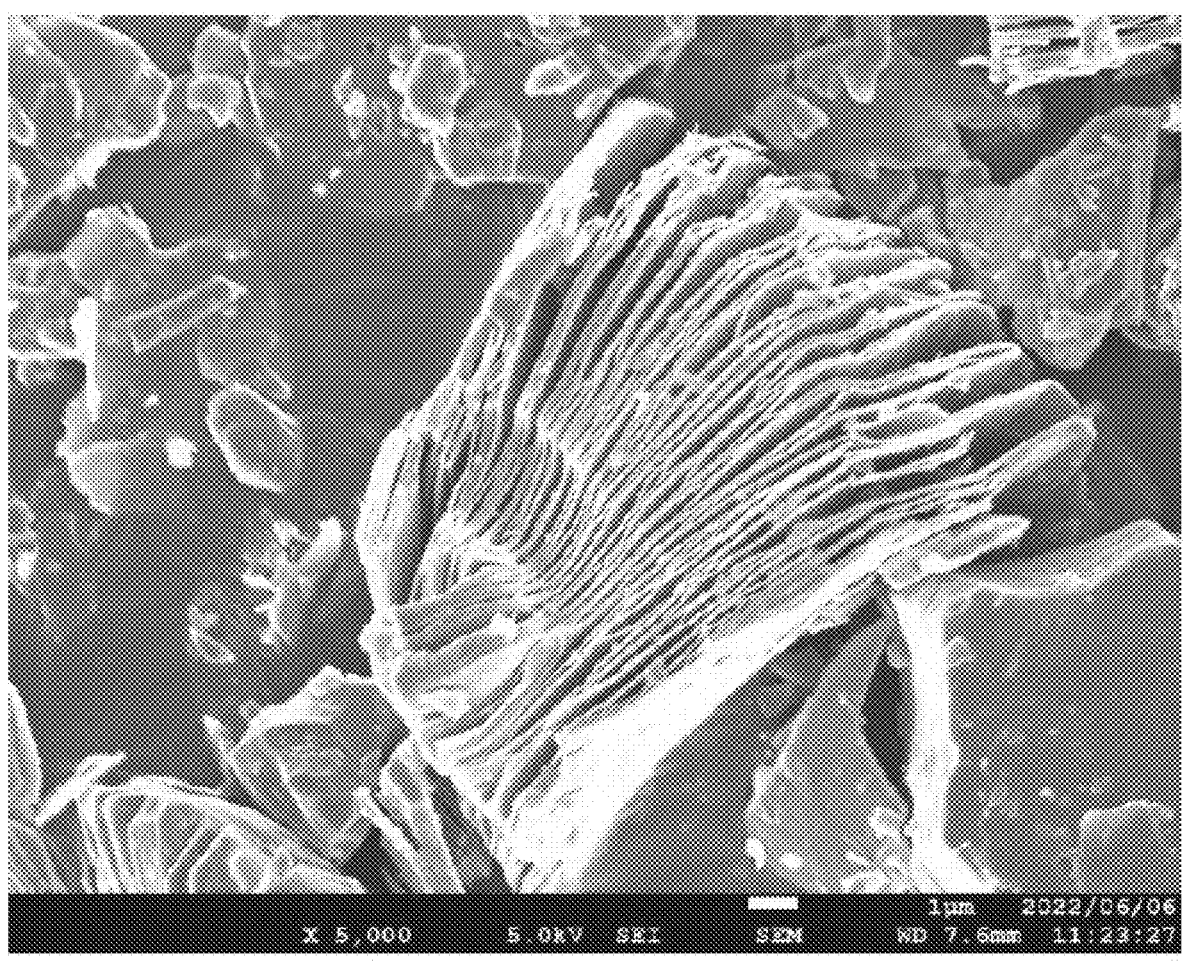
FIG. 13 is an SEM image of the inorganic compound in Comparative Example 3.
Figure 14:
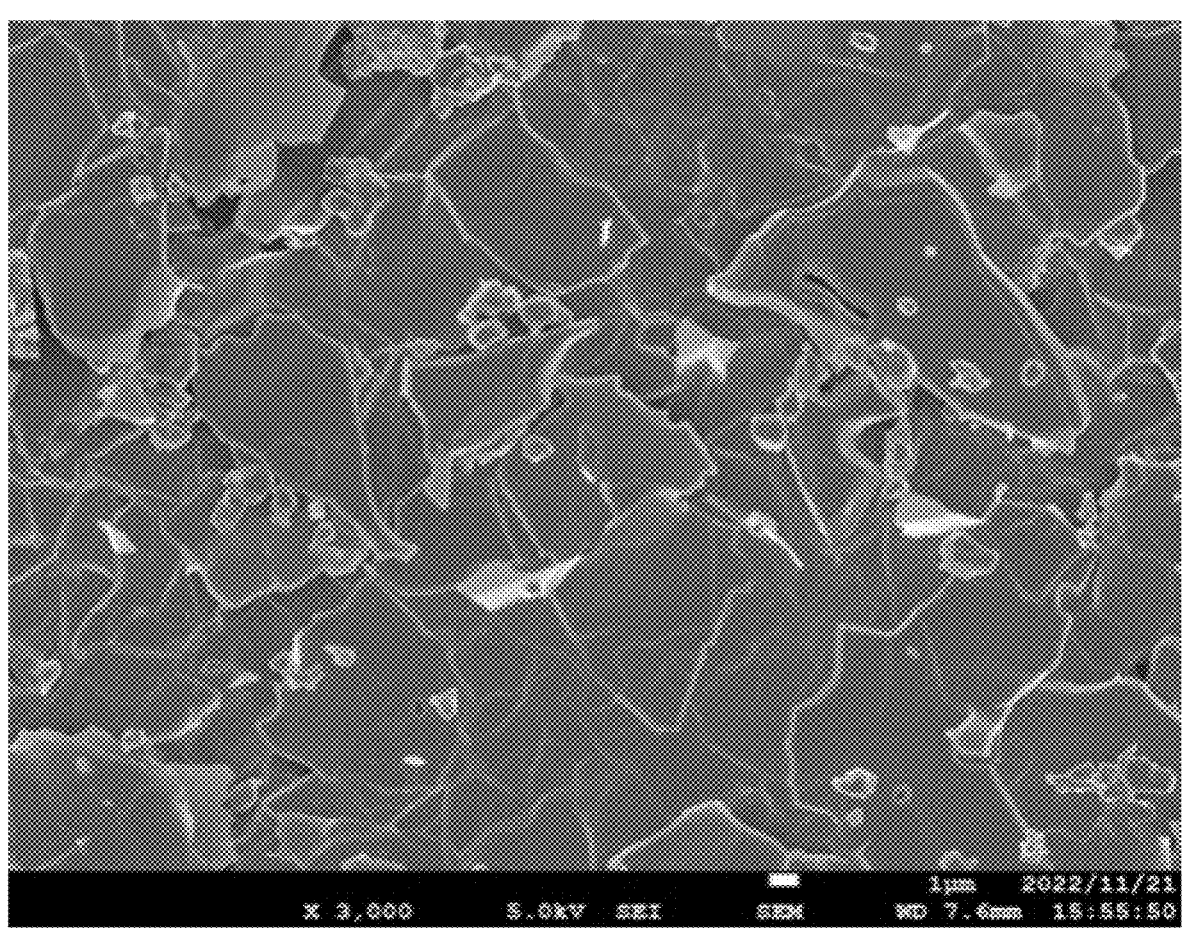
FIG. 14 is an SEM image of the inorganic compound in Comparative Example 5.

FIG. 5 is TG data of the inorganic compound of Example 1, and FIG. 6 is TG data of the inorganic compound of Comparative Example 1. In addition, FIG. 7 is XRD data of the inorganic compound of Example 1. Furthermore, FIG. 8 is an SEM image of the inorganic compound of Example 4, FIG. 9 is an SEM image of the inorganic compound of Example 7, FIG. 10 is an SEM image of the inorganic compound of Example 10, FIG. 11 is an SEM image of the inorganic compound of Comparative Example 1, FIG. 12 is an SEM image of the inorganic compound of Comparative Example 2, FIG. 13 is an SEM image of the inorganic compound of Comparative Example 3, and FIG. 14 is an SEM image of the inorganic compound of Comparative Example 5.

As shown in the above results, in the inorganic compounds of Examples 1 to 11, O, F and M which is one or more kinds of transition metal elements were included, and the (b/c) and the half-value width of the diffraction peak of the (110) plane were each controlled to within the predetermined range, so that the heat resistance was superior. On the other hand, in Comparative Examples 1 to 6, since at least one of the (b/c) or the half-value width of the diffraction peak of the (110) plane was outside the predetermined range, the heat resistance was poor. In addition, when comparing Example 6 and Comparative Example 2 with each other, although the values of (b/c) are close to each other, in Comparative Example 2 in which the above half-value width was 0.62°, the weight reduction upon heating at 1000° C. was 17.3%; whereas, in Example 6 in which the half-value width was 0.50°, the weight reduction was 8.9%, and thus the heat resistance of Example 6 was higher. From this, it can be considered that the heat resistance becomes higher when the half-value width is 0.60° or less. In addition, regarding the weight ratios of HF of Comparative Examples 5 and 6 in Table 2, since Comparative Examples 5 and 6 were treated with the aqueous solution of tetramethylammonium hydroxide rather than the HF aqueous solution, it is considered that fluorine ions detected in the measurement of the weight ratio of HF were not derived from the HF aqueous solution.

In addition, the powdered inorganic compound obtained in Example 1 was added to ethanol and stirred to obtain a dispersion containing the inorganic compound. Subsequently, the dispersion was applied to a glass plate, and then the solvent was evaporated to obtain a film containing the inorganic compound. In the same manner, a film containing the inorganic compound was obtained using the powdered inorganic compound obtained in Comparative Example 1.

As a result of measuring the heat resistance of these films in the same manner as described above, the heat resistance of the film obtained using the inorganic compound of Example 1 was superior to that of Comparative Example 1.

Example 12

To 50 g of a 50.0% HF aqueous solution, 5 g of $Ti_3C_2Al$ powder was added while stirring. After the $Ti_3C_2Al$ powder was added, the solution temperature was raised to 60° C. and stirred for 3 hours. Thereafter, the reaction solution was filtered, and the filtered product was repeatedly washed with distilled water until the filtrate became neutral. The filtered product after washing was dried at 150° C. for 24 hours under a nitrogen atmosphere to obtain the MXene that is the inorganic compound of Example 12. Each condition is shown in Table 3.

Example 13

To 30 g of a 25.0% HF aqueous solution, 5 g of $Ti_3C_2Al$ powder was added while stirring. After the $Ti_3C_2Al$ powder was added, the solution temperature was raised to 70° C. and stirred for 5 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Example 13.

Comparative Examples 7 to 8

MXenes which are the inorganic compounds of Comparative Examples 7 to 8 were obtained in the same manner as in Example 12, except for changing to the conditions shown in Table 3.

Examples 14 to 17, and Comparative Examples 9 and 10

MXenes which are the inorganic compounds of Examples 14 to 17 and Comparative Examples 9 and 10 were obtained in the same manner as in Example 13, except for changing to the conditions shown in Table 3.

Comparative Example 11

To a removal solution obtained by mixing 32.61 g of a 46% HF aqueous solution, 120 g of 37% hydrochloric acid and 47.39 g of distilled water, 10 g of $Ti_3C_2Al$ powder was added while stirring. After the $Ti_3C_2Al$ powder was added, the solution temperature was raised to 35° C. and stirred for 24 hours. Thereafter, the reaction solution was filtered, and the filtered product was repeatedly washed with distilled water until the filtrate became neutral. The filtered product after washing was dried under reduced pressure at 80° C. for 24 hours using a reduced-pressure dryer to obtain the MXene that is the inorganic compound of Comparative Example 11.

Comparative Example 12

To 100 g of a 7.5% HF aqueous solution, 5 g of $Ti_3C_2Al$ powder was added while stirring. After the $Ti_3C_2Al$ powder was added, the solution temperature was raised to 35° C. and stirred for 24 hours. Thereafter, the reaction solution was filtered, and the filtered product was repeatedly washed with distilled water until the filtrate became neutral. The filtered product after washing was dried using a tube furnace at 150° C. for 24 hours under a nitrogen atmosphere, and then calcined at 400° C. for 1 hour under a nitrogen atmosphere to obtain the MXene that is the inorganic compound of Comparative Example 12.

was defined as "Wm" and the molar ratio of the additive element was defined as "Wi". The molar ratio (Wi/Wm) was determined by dividing the molar ratio of the additive element by the molar ratio of M. The SEM-EDX measurement conditions are as follows.

Apparatus: JED-2300 (JEOL Ltd.)

Acceleration voltage: 20 kV

[4] Layer Thickness

Observation of the shape of the inorganic compound and the thickness measurement of the layer were performed by SEM observation. For the thickness of the layer, 20 samples of a flat particle in the image were randomly selected and the thickness thereof was measured, and the average value thereof was taken as the thickness of the layer. A TSM-7610F (JEOL Ltd.) was used for SEM measurement.

TABLE 3

| | Inorganic compound | HF concentration (%) | Removal solution amount (g) | Reaction time (h) | Reaction temperature (° C.) | Drying atmosphere | Drying temperature (° C.) |
|---|---|---|---|---|---|---|---|
| Example 12 | MXene | 50.0 | 50 | 3 | 60 | Nitrogen | 150 |
| Example 13 | MXene | 25.0 | 30 | 5 | 70 | Reduced pressure | 80 |
| Example 14 | MXene | 25.0 | 100 | 5 | 60 | Reduced pressure | 80 |
| Example 15 | MXene | 25.0 | 100 | 24 | 35 | Reduced pressure | 80 |
| Example 16 | MXene | 25.0 | 100 | 5 | 35 | Reduced pressure | 80 |
| Example 17 | MXene | 7.5 | 100 | 24 | 60 | Reduced pressure | 80 |
| Comparative Example 7 | MXene | 7.5 | 100 | 24 | 35 | Nitrogen | 150 |
| Comparative Example 8 | MXene | 25.0 | 30 | 24 | 45 | Nitrogen | 150 |
| Comparative Example 9 | MXene | 10.0 | 100 | 24 | Room temperature | Reduced pressure | 80 |
| Comparative Example 10 | MXene | 7.5 | 333 | 24 | 35 | Reduced pressure | 80 |

[Measurement and Evaluation]

The inorganic compounds obtained in Examples 12 to 17 and Comparative Examples 7 to 12 were subject to the below measurements and evaluations. The results are shown in Table 4.

[1] Molar Ratio a of M, Molar Ratio b of O, and Molar Ratio c of F

Elemental analysis of the inorganic compound was performed by SEM-EDX measurement, and the molar ratio (at %) of each element was determined. The molar ratio of M was defined as "a", the molar ratio of O was defined as "b", and the molar ratio of F was defined as "c". The molar ratio of O was divided by the molar ratio of F to obtain (b/c), and the sum of the molar ratio of O and the molar ratio of F was divided by the molar ratio of M to obtain (b+c)/a. The SEM-EDX measurement conditions are as follows.

Apparatus: JED-2300 (JEOL Ltd.)

Acceleration voltage: 20 kV

[2] Half-Value Width of Diffraction Peak of (110) Plane

The X-ray diffraction pattern of the inorganic compound was obtained by XRD measurement, and the half-value width of the diffraction peak of the (110) plane was obtained. The XRD measurement conditions are as follows.

Apparatus: fully-automated horizontal multipurpose X-ray diffractometer, SmartLab (Rigaku Corp.)

X-ray tube bulb: Cu

X-Ray Output: 40 kV, 50 mA

Filter: Cu_Kβ

Sample Preparation Method: filled to silicon non-reflective plate

[3] Ratio (Wi/Wm)

Elemental analysis of the inorganic compound was performed by SEM-EDX measurement, and the molar ratio (at %) of each element was determined. The molar ratio of M

[5] Weight Ratio of HF

The weight ratio of HF in the inorganic compound was calculated by mixing 10 g of acetonitrile and 1 g of the inorganic compound, stirring the mixture for 24 hours, followed by quantifying the F ion concentration in the acetonitrile by ion chromatography measurement, calculating the weight (g) of HF eluted in the acetonitrile, and dividing the weight of HF by 1 g of the weight of the inorganic compound.

[6] Weight Ratio of moisture

The weight ratio of the moisture in the inorganic compound was calculated by mixing 10 g of acetonitrile and 1 g of the inorganic compound, stirring the mixture for 24 hours, followed by quantifying the moisture amount in the acetonitrile by a Karl Fischer moisture meter, and dividing the moisture amount by 1 g of the weight of the inorganic compound.

[7] Generated Amounts of Methane and Hydrogen

In a glove box filled with inert gas (Ar, He or nitrogen), 1 g of the inorganic compound was placed in a 20 ml headspace vial, and the cap was closed. The sample was allowed to stand still in the dark at room temperature for several days. Next, the gas in the vial was collected by a syringe, the gas component was quantitatively evaluated by GC-BID measurement, and the amounts of methane and hydrogen in the vial were calculated. By dividing the amounts of methane and hydrogen by the number of days of standing, the amounts of methane and hydrogen (nmol/g/day) generated in one day by 1 g of the inorganic compound were calculated.

TABLE 4

| | M | X | Y | Additive element | Ratio (Wi/Wm) | (b/c) | ((b + c)/a) | Half-value width (°) | Layer thick-ness (nm) | Weight ratio of HF (ppm) | Weight ratio of moisture (ppm) | Methane generation amount (room temperature, in inert gas) (nmol/g/day) | Hydrogen generation amount (room temperature, in inert gas) (nmol/g/day) |
|---|---|---|---|---|---|---|---|---|---|---|---|---|---|
| Example 12 | Ti | C | H | Al | 0.076 | 0.47 | 1.33 | 0.67 | 82 | 10 | 3532 | 14 | 21 |
| Example 13 | Ti | C | H | Al | 0.077 | 0.75 | 1.52 | 0.62 | 110 | 10 | 1241 | 10 | 15 |
| Example 14 | Ti | C | h | Al | 0.09 | 0.58 | 1.64 | 0.62 | 103 | 10 | 879 | 9 | 14 |
| Example 15 | Ti | C | H | Al | 0.004 | 1.02 | 0.85 | 0.46 | 180 | 10 | 387 | 3 | 5 |
| Example 16 | Ti | C | H | Al | 0.027 | 0.79 | 1.54 | 0.50 | 175 | 10 | 401 | 3 | 5 |
| Example 17 | Ti | C | H | Al | 0.006 | 1.34 | 0.69 | 0.55 | 155 | 10 | 355 | 4 | 6 |
| Comparative Example 7 | Ti | C | H | Al | 0.015 | 1.67 | 0.94 | 0.47 | 212 | 10 | 132 | Less than detection limit of apparatus | Less than detection limit of apparatus |
| Comparative Example 8 | Ti | C | H | Al | 0.022 | 1.44 | 1.05 | 0.43 | 151 | 10 | 301 | Less than detection limit of apparatus | Less than detection limit of apparatus |
| Comparative Example 9 | Ti | C | H | Al | 0.016 | 2.00 | 1.27 | 0.48 | 250 | 10 | 118 | Less than detection limit of apparatus | Less than detection limit of apparatus |
| Comparative Example 10 | Ti | C | H | Al | 0.001 | 0.67 | 0.48 | 0.35 | 235 | 10 | 203 | Less than detection limit of apparatus | Less than detection limit of apparatus |
| Comparative Example 11 | Ti | C | H, Cl | Al | 0.008 | 1.22 | 1.38 | 0.38 | 240 | 10 | 421 | Less than detection limit of apparatus | Less than detection limit of apparatus |
| Comparative Example 12 | Ti | C | H | Al | 0.013 | 2.23 | 0.96 | 0.47 | 212 | 10 | 107 | Less than detection limit of apparatus | Less than detection limit of apparatus |

Figure 15:
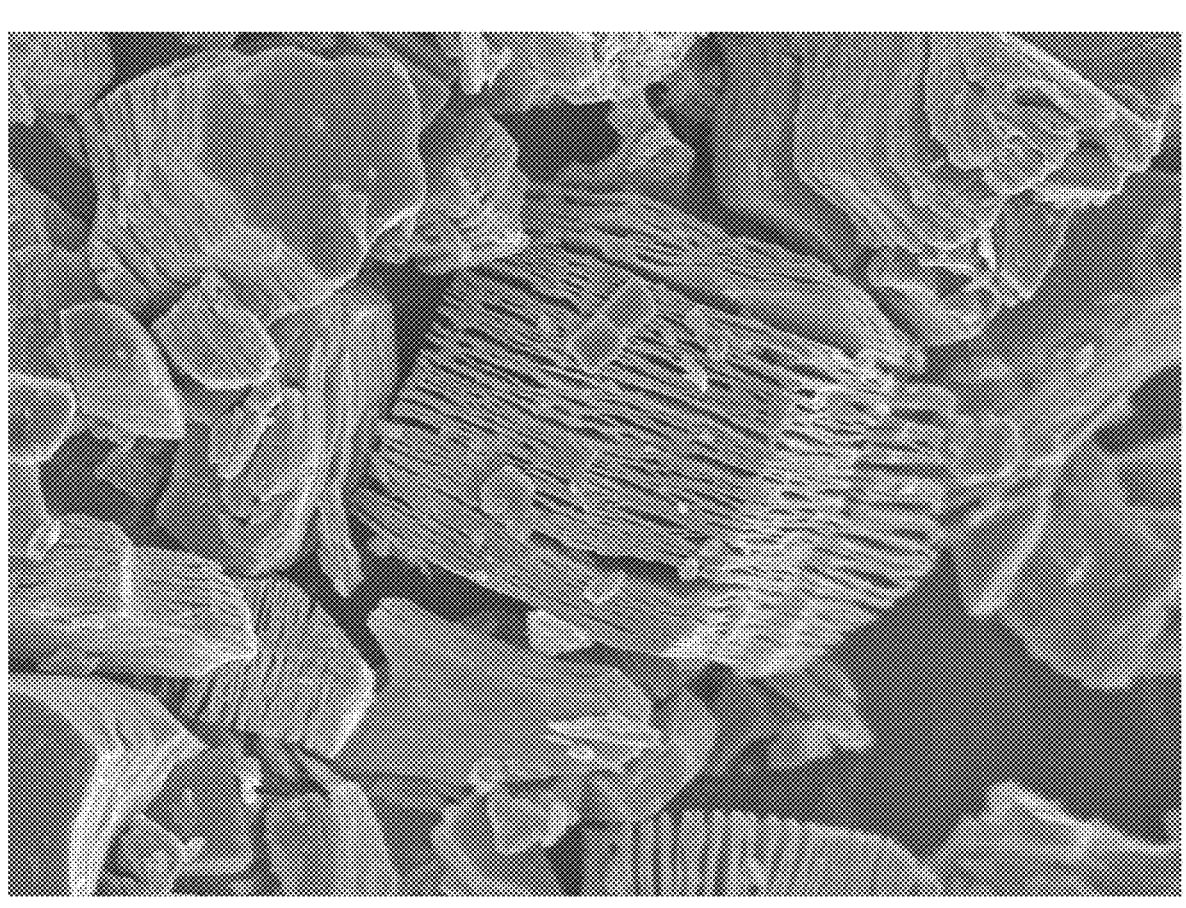
FIG. 15 is an SEM image of the inorganic compound in Example 12.
Figure 16:
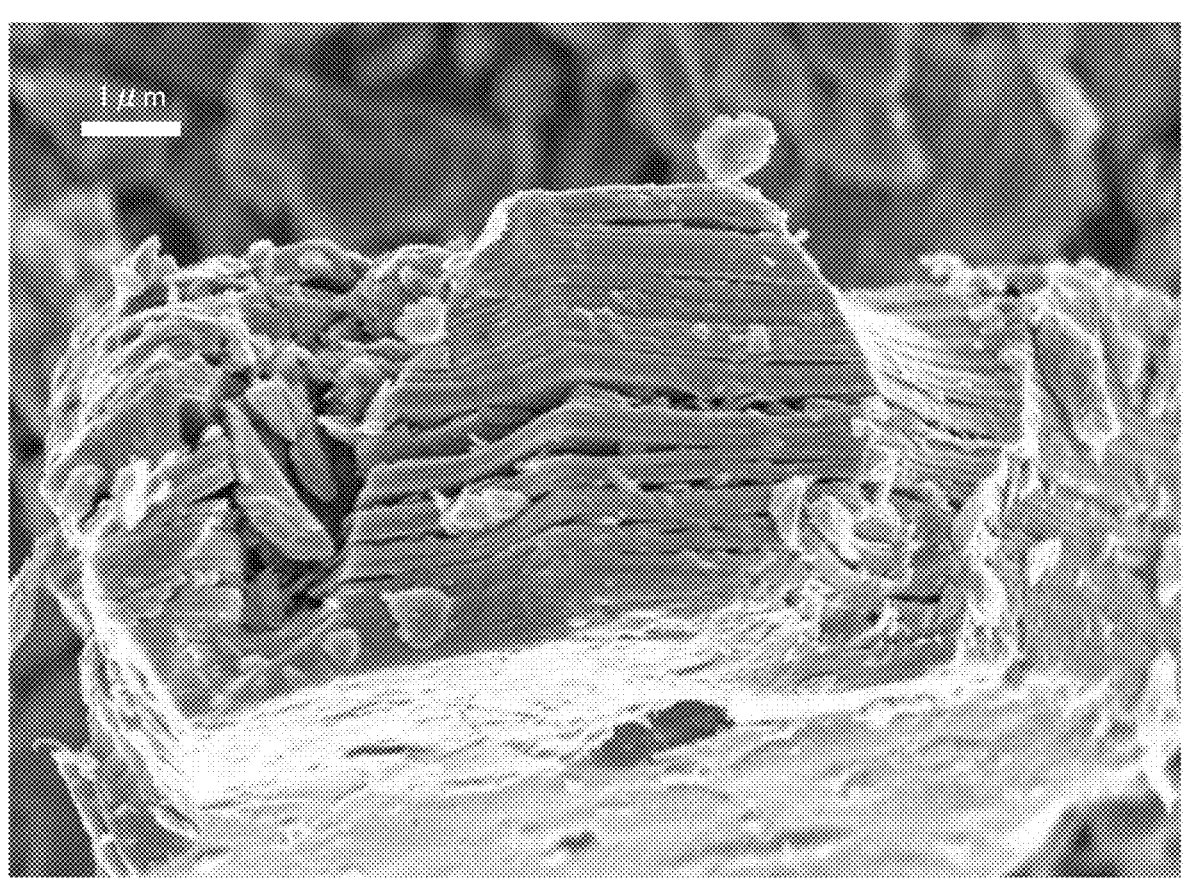
FIG. 16 is an SEM image of the inorganic compound in Comparative Example 9.
Figure 17:
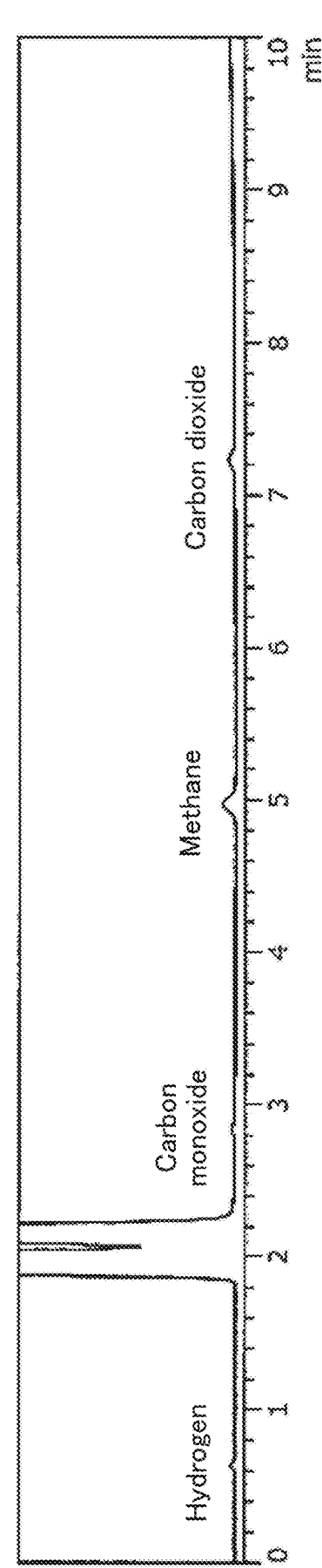
FIG. 17 is GC-BID data of the inorganic compound in Example 12.
Figure 18:
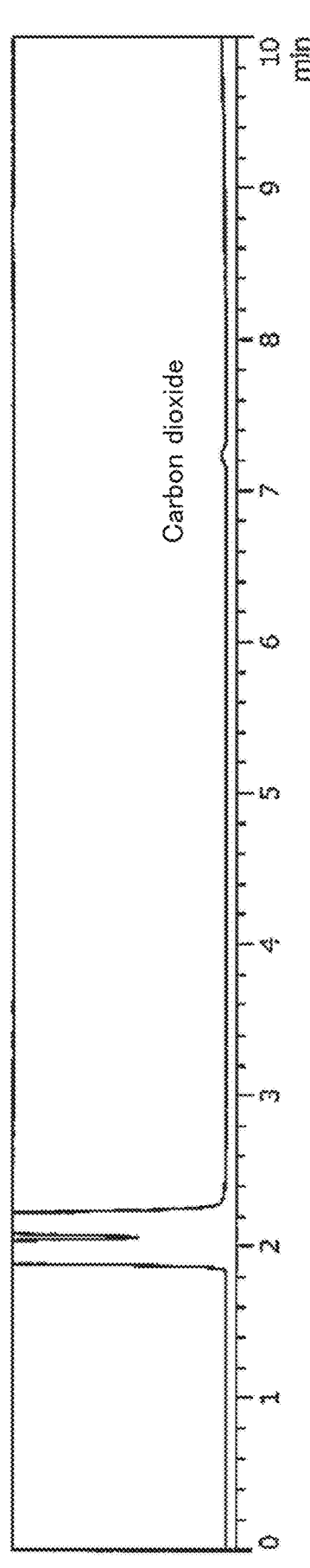
FIG. 18 is GC-BID data of the inorganic compound in Comparative Example 9.
Figure 19:
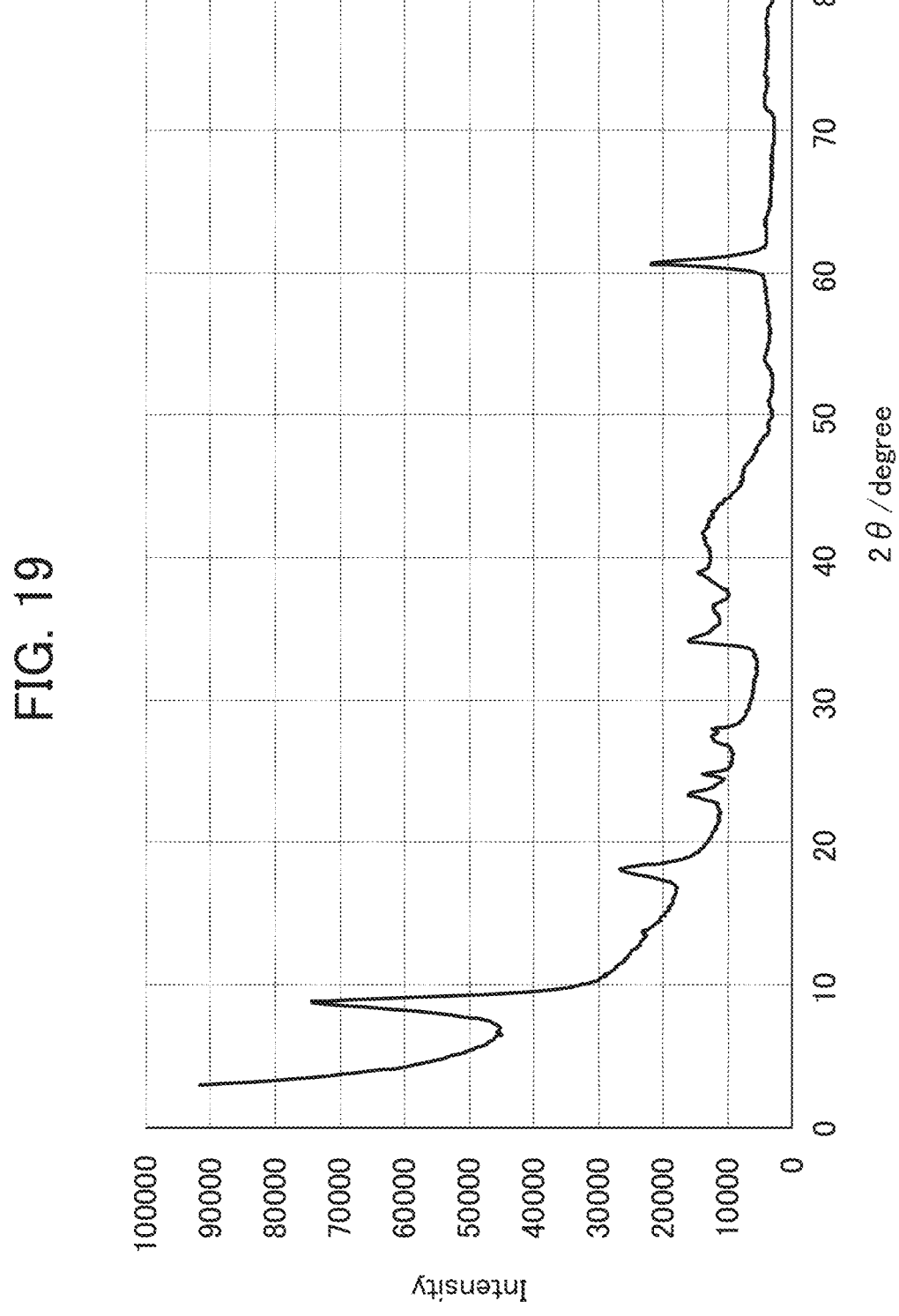
FIG. 19 is XRD data of the inorganic compound in Example 12.
Figure 20:
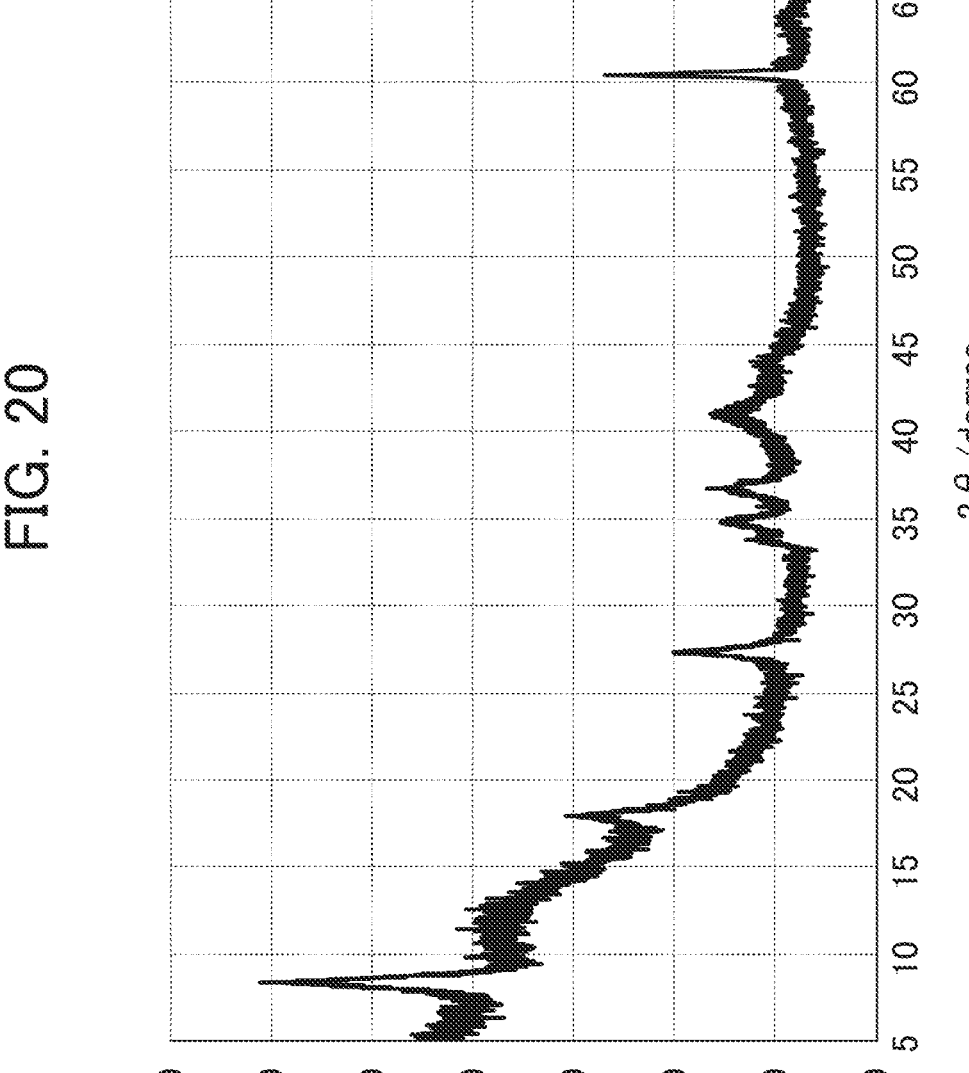
FIG. 20 is XRD data of the inorganic compound in Comparative Example 9.

FIG. 15 is an SEM image of the inorganic compound of Example 12, and FIG. 16 is an SEM image of the inorganic compound of Comparative Example 9. In addition, FIG. 17 is GC-BID data of the inorganic compound of Example 12, and FIG. 18 is GC-BID data of the inorganic compound of Comparative Example 9. Further, FIG. 19 is XRD data of the inorganic compound of Example 12, and FIG. 20 is XRD data of the inorganic compound of Comparative Example 9.

As shown in the above results, in the inorganic compounds of Examples 12 to 17, O, F and M which is one or more kinds of transition metal elements were included, and the (b/c) and the half-value width of the diffraction peak of the (110) plane were each controlled to be within the predetermined range, so that the generation of methane and hydrogen at a low temperature was excellent. On the other hand, in Comparative Examples 7 to 12, the generation of methane and hydrogen at a low temperature was not confirmed.

In addition, the powdered inorganic compound obtained in Example 12 was added to ethanol and stirred to obtain a dispersion containing the inorganic compound. Subsequently, the dispersion was applied to a glass plate, and then the solvent was evaporated to obtain a film containing the inorganic compound. In the same manner, a film containing the inorganic compound was obtained using the powdered inorganic compound obtained in Comparative Example 7.

As a result of measuring the generated amounts of methane and hydrogen for these films in the same manner as described above, the film obtained using the inorganic compound of Example 12 was superior to Comparative Example 7 in the generations of methane and hydrogen at a low temperature.

The invention claimed is:

1. An inorganic compound comprising M, O and F, wherein

M is one or more kinds of transition metal elements, when defining a molar ratio of O as "b" and defining a molar ratio of F as "c", (b/c) is 0.60 or more and 2.30 or less, and a half-value width of a diffraction peak of a (110) plane obtained by X-ray diffraction analysis is 0.60° or less.

2. The inorganic compound according to claim 1, further comprising X, wherein X is one or more kinds of elements selected from C and N.

3. The inorganic compound according to claim 2, wherein M is at least one of a group 4 element or a group 5 element in the periodic table, and X is C.

4. The inorganic compound according to claim 2, wherein M is at least one of Ti or Nb, and X is C.

5. The inorganic compound according to claim 1, further comprising X and Y, wherein X is one or more kinds of elements selected from C and N, and Y is one or more kinds of elements selected from the group consisting of H, an alkali metal element, an alkaline earth metal element, a chalcogen element excluding oxygen, and a halogen element excluding fluorine.

6. The inorganic compound according to claim 5, wherein M is at least one of a group 4 element or a group 5 element in the periodic table, and X is C.

7. The inorganic compound according to claim 5, wherein M is at least one of Ti or Nb, and X is C.

8. The inorganic compound according to claim 1, further comprising one or more kinds of inevitable impurities selected from the group consisting of Al, Si, Ga, P, S, Ge, As, Cd, In, Sn, Tl and Pb, wherein a ratio (Wi/Wm) of a total molar amount Wi of the inevitable impurities relative to a total molar amount Wm of M is $1.0 \times 10^{-6}$ or more and $5.0 \times 10^{-1}$ or less.

9. The inorganic compound according to claim 1, wherein, when defining a molar ratio of M in the inorganic compound as "a", ((b+c)/a) is 0.30 or more.

10. The inorganic compound according to claim 1, wherein, when defining a molar ratio of M in the inorganic compound as "a", ((b+c)/a) is 1.60 or less.

11. The inorganic compound according to claim 1, wherein the inorganic compound is in a layered form, and a thickness of a layer thereof is 0.15 μm or more and 10.00 μm or less.

12. The inorganic compound according to claim 1, wherein a weight ratio of HF in the inorganic compound relative to a total amount of the inorganic compound is 1 ppt or more and 50 ppm or less.

13. The inorganic compound according to claim 1, wherein a weight ratio of moisture in the inorganic compound relative to a total amount of the inorganic compound is 1 ppm or more and 1.0% or less.

14. The inorganic compound according to claim 1, wherein the inorganic compound is a MXene.

15. A dispersion comprising the inorganic compound according to claim 14.

16. A film comprising the inorganic compound according to claim 14.

17. A method for producing a dispersion, comprising producing the dispersion using the inorganic compound according to claim 14.

18. A method for producing a film, comprising producing the film using the inorganic compound according to claim 14.

\* \* \* \* \*